United States Patent [19]
Reddy et al.

[11] Patent Number: 5,639,639
[45] Date of Patent: *Jun. 17, 1997

[54] RECOMBINANT HETERODIMERIC HUMAN FERTILITY HORMONES, AND METHODS, CELLS, VECTORS AND DNA FOR THE PRODUCTION THEREOF

[75] Inventors: Vermuri B. Reddy, Westboro; Nancy Hsiung, Wellesley, both of Mass.; Anton K. Beck, Pfeffiagen, Switzerland; Edward George Bernstine, Boston, Mass.

[73] Assignee: Genzyme Corporation, Boston, Mass.

[*] Notice: The portion of the term of this patent subsequent to Jun. 20, 2006, has been disclaimed.

[21] Appl. No.: 268,734

[22] Filed: Jun. 30, 1994

Related U.S. Application Data

[63] Continuation of Ser. No. 515,481, Apr. 27, 1990, abandoned, which is a continuation-in-part of Ser. No. 323,772, Mar. 15, 1989, abandoned, and Ser. No. 696,647, Jan. 30, 1985, Pat. No. 4,923,805, which is a continuation-in-part of Ser. No. 548,228, Nov. 2, 1983, Pat. No. 4,840,896, said Ser. No. 323,772, is a continuation of Ser. No. 548,228.

[51] Int. Cl.$^6$ ........................................... C12N 15/16
[52] U.S. Cl. ................... 435/69.4; 435/320.1; 435/325; 435/354; 435/363; 435/365.1
[58] Field of Search ..................... 530/399; 435/69.4, 435/69.8, 172.1, 172.3, 240.2, 252.3, 320.1; 536/23.51; 935/9, 34, 44

[56] References Cited

U.S. PATENT DOCUMENTS

| | | | |
|---|---|---|---|
| 4,363,877 | 12/1982 | Goodman et al. | 435/320.1 |
| 4,383,034 | 5/1983 | Sugimoto | 435/70.2 |
| 4,383,035 | 5/1983 | Sugimoto | 435/70.2 |
| 4,383,036 | 5/1983 | Sugimoto | 435/70.2 |
| 4,394,443 | 7/1983 | Weissman et al. | 435/6 |
| 4,401,759 | 8/1983 | Rubin et al. | 435/91.51 |
| 4,405,712 | 9/1983 | Vandewoude et al. | 435/5 |
| 4,416,988 | 11/1983 | Rubin | 435/91.51 |
| 4,419,446 | 12/1983 | Howley et al. | 435/69.1 |
| 4,442,205 | 4/1984 | Hamer et al. | 435/69.3 |
| 4,468,464 | 8/1984 | Cohen et al. | 435/320.1 |
| 4,656,134 | 4/1987 | Ringold | 435/91 |
| 4,704,362 | 11/1987 | Itakura et al. | 435/252.3 |
| 4,717,670 | 1/1988 | Beck | 435/320.1 |
| 4,816,397 | 3/1989 | Boss et al. | 435/69.6 |
| 4,840,896 | 6/1989 | Reddy et al. | 435/69.4 |
| 4,923,805 | 5/1990 | Reddy et al. | 435/69.4 |

FOREIGN PATENT DOCUMENTS

| | | |
|---|---|---|
| 1128440 | 7/1982 | Canada. |
| 021468 | 1/1981 | European Pat. Off.. |
| 043718 | 1/1982 | European Pat. Off.. |
| 045573 | 2/1982 | European Pat. Off.. |
| 060057 | 9/1982 | European Pat. Off.. |
| 073656 | 3/1983 | European Pat. Off.. |
| 078154 | 5/1983 | European Pat. Off.. |
| 088632 | 9/1983 | European Pat. Off.. |
| 089666 | 9/1983 | European Pat. Off.. |
| 091527 | 10/1983 | European Pat. Off.. |
| 091539 | 10/1983 | European Pat. Off.. |
| 093619 | 11/1983 | European Pat. Off.. |
| 116201 | 6/1984 | European Pat. Off.. |
| 120694 | 10/1984 | European Pat. Off.. |
| 2565599 | 12/1985 | France. |
| 2091271 | 7/1982 | United Kingdom. |
| 2116183 | 9/1983 | United Kingdom. |
| 2137631 | 10/1984 | United Kingdom. |
| WO81/02426 | 9/1981 | WIPO. |
| WO82/00158 | 1/1982 | WIPO. |
| WO83/01783 | 5/1983 | WIPO. |
| WO85/01958 | 5/1985 | WIPO. |
| WO85/01959 | 5/1985 | WIPO. |
| WO86/04589 | 8/1986 | WIPO. |

OTHER PUBLICATIONS

Rathnam et al. (1975) The Journal of Biological Chemistry vol. 250 (No. 17), pp. 6735–6746.
Saxena et al. (1976) The Journal of Biological Chemistry vol. 251 (No. 4), pp. 993–1005.
The Merck Index, Stecher et al Merck & Co., Inc. 1052 (1968).
Biotech Newswatch, :7 (Mar. 7, 1983).
Biotech Newswatch, :3 (Jan. 16, 1984).
Biotech Newswatch, :3–4 (Jun. 20, 1983).
Biotechnology, :753–755 (1984).
Chem. Eng. News, 61:41 (Nov. 21, 1983).
Genetic Eng. Letter, :4 (Aug. 10, 1984).
Genetic Eng Letter, :4 (Dec. 10, 1983).
Genetic Tech News, :7 (1983).
Genetic Tech News, :9 (1982).
Genetic Tech News, :1 (Dec. 1983).
Genetic Tech. News, 2:3 (1982).
Scrip, 877:18 (Mar. 7, 1984).
(transl'n of) Judgement dated Apr. 1, 1993 of the Court of Appeal in the Hague (Applied Research Systems v. Organon), 1993.
Agrawal et al., J. Gen. Virol., 73:201–206 (1992).
Albert et al, J Clin Endocrinol Metab, 28:1214–1219 (Aug. 1968).
Allshire et al, J. Mol. Biol., 188:1–13 (1986).
Allshire et al, Virus Research, 6:141–154 (1986).
Amtmann et al., J Virol, 35:962–964 (Aug. 1980).
Anderson et al, PNAS, 78:5598–5602 (Sep. 1981).
Anderson et al., PNAS, 80:6838–6842 (Nov. 1983).
Anfinsen, Science, 181:223–230 (1973).
Ashitaka, Acta Obst et Gyn Jap, 17:124–135 (1970).

(List continued on next page.)

*Primary Examiner*—Stephen G. Walsh
*Assistant Examiner*—Lorraine M. Spector
*Attorney, Agent, or Firm*—Browdy and Neimark

[57] ABSTRACT

Biologically active heterodimeric human fertility hormones composed of two different subunits, each subunit being synthesized in the same cell transformed by at least one cell expression vector having heterologous DNA encoding each subunit with each subunit being controlled by a separate promoter. Preferred human fertility hormones include hCG, hLH and hFSH.

26 Claims, 13 Drawing Sheets

OTHER PUBLICATIONS

Ashitaka et al, Endocrinol, 87:233–244 (1970).
Ashitaka et al, Endocrinol, 90:609–617 (1972).
Asselbergs et al, Eur J Biochem, 91:65–72 (1978).
Bahl et al, Biochem Biophys Res Comm, 48:416–422 (1972).
Banerji et al, Cell, 27:299–308 (1981).
Barr et al, J Endocr, 38:395–399 (1967).
Beck et al., 7th Int'l Cong Endoc, :308 (19840.
Beck et al., DNA, 4:76 (Jan.21, 1985).
Bellisario et al, J Biol Chem, 248:6796–6809 (1973).
Bendig, Protein Production of Biotech., Harris et al 79–98 (1990).
Bergman et al., Gene, 50:185–193 (1986).
Blattner et al., Science, 196:161–169 (1977).
Bogdanove et al., Endo, 95:219–228 (1974).
Borth et al, Archiv fur Gynakologie, 188:497–538 (1957) in German, no translation.
Boulianne et al., Nature, 312:643–646 (Dec. 13, 1984).
Braunstein et al, Annals Int Med, 78:39–45 (1973).
Braunstein et al, Biochem Biophys Res Comm, 42:962–967 (1971).
Breathnach, EMBO J, 3:901–908 (1984).
Brennand et al, J Biol Chem, 258:9593–9596 (1983).
Brown, Aust N Z J Obstet Gynaec, 18:47–54 (1978).
Burke et al, Cell, 36:847–856 (Apr. 1984).
Burke et al, EMBO J, 3:551–556 (1984).
Burrell et al, Nature, 279:43–47 (1979).
Cabilly et al., PNAS, 81:3273–3277 (1984).
Carloni et al, Gene, 31:49–57 (1984).
Carlsen et al, J Biol Chem, 248:6810–6827 (1973).
Chappel et al., Endocrine Reviews, 4:179–211 (1983).
Chen et al, J Biol Chem, 257:14446–14452 (Dec. 10, 1982).
Chin et al, Endocrinol, 108:1628–1633 (1981).
Chou, PNAS, 75:1854–1858 (1978).
Christman et al, PNAS, 79:1815–1819 (1982).
Church et al, Proc Natl Acad Sci USA, 81:1991–1995 (Apr. 1984).
Closset et al., Eur. J. Biochem., 86:115–120 (1978).
Collen et al, J Pharmacol Exp Ther, 231:146–152 (1984).
Colman et al, Eur J Biochem, 113:339–348 (1981).
Corbani et al, Mol Cell Endocrinol, 35:83–87 (1984).
Counis et al, 7th Int'l Cong. Endocrinol: Abstracts, Excerpta Medica 448 (1984).
Cox et al, Am J Med Sci, 275:232–248 (1978).
Creighton, J Mol Biol, 144:521–550 (1980).
Cumming, Glycobiology, 1:115–130 (1991).
Davis et al., PNAS, 80:3976–80 (Jul. 1983).
Denniston et al, Gene, 32:357–368 (1984).
Derynck et al, Nucleic Acids Res, 11:1819— (1983).
Devos et al, Nucleic Acids Res, 10:2487–2501 (1982).
Di Maio, PNAS, 79:4030–4034 (1982)
DiMaio et al, Mol Cell Biol, 4:340–350 (Feb. 1984).
Doms et al, J Cell Biol, 5:179a (1983).
Dubois et al, PNAS, 77:4549–4553 (1980).
Dufau et al, Biochem Biophys Res Comm, 44:1022–1029 (1971).
Edwards et al, The Lancet, 2:1265–1269 (Dec. 3, 1983).
Elder et al, Ann Rev Genet, 15:295–340 (1981).
Faiman et al, J Clin Endo Metab, 27:444–447 (1967).
Faiman et al, New Eng J Med, 277:1395–1399 (1967).
Fathalla, The Lancet, 2:163 (1971).
Falkner et al, Nature, 298:286–288 (Jul. 15, 1982).
Fein et al, J Clin Endocr Metab, 50:1111–1120 (1980).
Fiddes et al, J. Mol. Appl. Genet., 1:3–18 (1981).
Fiddes et al, Nature, 281:351–356 (Oct. 04, 1979).
Fiddes et al, Nature, 286:684–687 (Aug. 14, 1980).
Fiers et al, Primary and Tertiary Structure . . . , Miwa et al Japan Sci Soc Press 227–236 (1982).
Flamigni et al, Contracept Fertil Sexual, 13:1097–1101 (1985).
Fujiki et al., J. Biol. Chem., 253:5363–5368 (1978).
Fukenaga, D R., PNAS 81:5086–5090 (Aug. 1984).
Garcia et al, Fertility and Sterility, 44:478–483 (Oct. 1985).
Garoff et al, J Cell Biol, 97:652–658 (1983).
Garoff et al, J Mol Biol, 124:587–600 (1978).
Garoff et al, Nature, 274:487–490 (1978).
Germain et al, Nature, 306:190–194 (Nov. 10, 1983).
Gething et al., Nature, 300:598–603 (Dec. 16, 1982).
Gheysen et al, J Mol Appl Genet, 1:385–394 (1982).
Ghosh et al, Am. J. Hum. Genet., 29:46A (1977).
Ghosh et al, Nature, 267:435–437 (1977).
Gibson et al, TIBS, 5:290–293 (1980).
Giudice et al, Biochem Biophys Acta, 533:140 (1978).
Giudice et al, J Biol Chem, 251:6392 (1976).
Gluzman, Cell, 23:175–182 (1981).
Godine et al, J Biol Chem, 255:8780–8783 (1980).
Goodenow et al, Nature, 301:388–394 (Feb. 3, 1983).
Gorman et al, PNAS, 79:6777–6781 (1982).
Gough et al, J Mol Biol, 162:43–67 (1982).
Goverman et al, J Biol Chem, 257:15059–15064 (Dec. 25, 1982).
Graham et al., Virology, 52:456–467 (1973).
Grantham et al., Nucl. Acids Research, 9:43–73 (1981).
Gray et al., Nature, 295:503–508 (Feb. 11, 1982).
Gruss et al, PNAS, 78:133–137 (1981).
Gunning et al, Cell, 36:709–715 (1984).
Gupta et al, J Biol Chem, 260:2941–2944 (1986).
Ham et al., Methods Enzymol, 58:44–93 (1979).
Hamer et al, J Mol Appl Gen, 1:273–288 (1982).
Hanover et al, Arch Biochem Biophys, 211:1–19 (1981).
Hartman et al, PNAS, 79:233–237 (Jan. 1982).
Heilman, Virology, 119:22–34 (1982).
Heine et al., J Gen Virol, 44:45–55 (1979).
Hitzeman et al, Nature, 293:717–722 (Oct. 29, 1981).
Hitzeman et al, Nucleic Acid Res, 11:2745–2763 (1983).
Howard, TIBS, :209–212 (1983).
Howley et al. Methods Enzymol. 101:387–402 (1983).
Hsiung et al, J Mol App Genet, 2:497–506 (1984).
Hsiung et al, Mol Cell Biol., 2:401–411 (1982).
Hsueh et al, Endocrine Rev, 5:76–127 (1984).
Hubbard et al, Ann Rev Biochem, 50:555–583 (1981).
Hussa et al, J Clin Endocri Metab, 46:6976 (1978).
Jaenicke, Biophys Struct Mech, 8:231–256 (1982).
Jaye et al., Nucl Acids Res, 11:2325–2335 (1983).
Jia et al, Neuroendocrinol, 41:445–448 (1985).
Jones et al, Fertil Steril, 38:14–21 (Jul. 1982).
Julius et al, Cell, 36:309–318 (1984).
Kaetzel et al, J Biol Chem, 263:6344–6351 (May 5, 1988).
Kaetzel et al, PNAS, 82:7280–7283 (Nov. 1985).
Kahn et al, New Eng J Med, 297:565–569 (1977).
Kalyan et al, J Biol Chem, 258:67–74 (Jan. 10, 1983).
Kao et al, PNAS, 60:1275–1281 (1968).
Karin et al, Cell, 36:371–379 (1984).
Kato, Mol Cell Endocrinol, 55:107–112 (1988).
Kaufman et al, J Mol Biol, 159:601–621 (1982).
Kaufman et al, Mol Cell Biol, 2:1304–1319 (1982).
Kaufman et al, Mol Cell Biol, 5:1750–1759 (Jul. 1985).
Keene et al, J. Biol. Chem., 264:4769–4775 (1989).

Kenigsberg et al, Fertility and Sterility, 42:116–126 (Jul. 1984).
Kenter et al, J Cell Biol, 98:2215–2221 (1984).
Keutmann et al, Biochem, 22:3067–3072 (1983).
Kimuri et al, Viology, 49:394–403 (1972).
Knobil, Recent Prog Horm Res, 36:53–88 (1980).
Knobil et al, Science, 207;1371–1373 (Mar. 21, 1980).
Kolata, Science, :805 (Feb. 24, 1984.).
Kondoh et al, Nature, 301:440 (1983).
Kondor–Koch et al, J Cell Biol, 97:644–651 (1983).
Kondor–Koch et al, PNAS, 79:4525–4529 (1982).
Kubo et al, Mol Immunol, 20:67–74 (1983).
Kushner et al, J. Mol. Appl. Gen., 1:527–538 (1982).
Laemmli, Nature, 227:680–685 (1970).
Lai et al, PNAS, 77:244–248 (1980).
Landefeld et al, Biochem Biophys Res Com, 90:1111–1118 (1979).
Lathe, R., J. Mol. Biol, 183:1–12 (1985).
Laub et al, J Biol Chem, 258:6043–6050 (May 25, 1983).
Law et al, Mol Cell Bio, 3:2110–2115 (1983).
Law et al., PNAS, 78:2727–2731 (May 1981).
Lawn et al., Cell, 15:1157–1174 (1978).
Leder et al., Science, 196:175–177 (1977).
Lester et al, Somatic Cell Genet, 6:241–259 (1980).
Levy, Curr Topics Microbiol Immun, 79:111–118 (1978).
Lieber et al., Science, 182:56–59 (1973).
Lieblich et al, Nature, 260:530–532 (1976).
Liu et al, DNA, 1:213–221 (1982).
Lowy et al, J Virol, 26:291–298 (1978).
Lowy et al, Nature, 287:72–74 (1980).
Lubiniecki et al, Develop Biol Standard, 60:141–146 (1985).
Lupker et al, Gene, 24:281–287 (1983).
Lusky et al., Eukaryotic Viral Vectors, Glutzman Cold Spr Hrbr Labs 99–107 (1982).
Lusky et al, Nature, 293:79–81 (Sep. 3, 1981).
Lustbader et al, 68th Mtg. Endo Soc., :Abst No 513 (1986).
Lustbader et al., 7th Int'l Cong Endoc, :863 (1984).
Manjunath et al, Mol Cell Endocrinol, 28:125–138 (1982).
Manly et al., J Gen Virol, 39:505–517 (1978).
Mannaerts et al, Endocrinology, 129:2623–2630 (1991).
Marshall, Ann Rev Biochem, 41:673–702 (1972).
Matthais et al., J. Mol. Biol., 187:557–568 (19860.
Maurer et al, J Biol Chem, 253:6315–6318 (1978).
Mayo et al, Cell, 29:99–108 (1982).
Melmed, J Clinical Endo Metab, 56:1145–1151 (1983).
Meyer et al, Inst Molekularbiol I, 36:752 (1980).
Michel et al, Biotechnology, 3:561–566 (1985).
Midgley, J Clin Endocrinol & Metab, 27:295–299 (1967).
Mishina et al, Nature, 307:604–608 (Feb. 16, 1984).
Mitrani–Rosenbaum et, Mol Cell Biol, 3:233–240 (1983).
Mitrani–Rosenbaum et, Virus Research, 8:335–347 (1987).
Miyanohara et al, PNAS, 80:1–5 (1983).
Morell et al., J Biol Chem, 246:1461–1467 (1971).
Morgan et al, J Biol Chem, 250:5247–5258 (1975) hcg sequence (L & Z).
Morgan et al, J of Biological Chemistry, 13:5247–5258 (1975).
Moriarty et al., PNAS, 78:2606–2610 (Apr. 1981).
Morrison et al, Ann Rev Immunol, 2:239–256 (1984).
Moyle et al, J Bio Chem, 250:9163–9169 (1975).
Mulligan et al, Nature, 277:108–114 (1979).
Neufeld et al, Biochem Glycoproteins and Proteoglycans, Lennarz Plenum Press 241–266 (1980).
Nilson et al, J Reprod Fert, Suppl, 34:227–236 (1987).
Nishikawa et al, Biochem Biophys Res Com, 87:1235–1242 (1979).
Ochi et al, Nature, 302:340–342 (Mar. 24, 1983).
Ochi et al., PNAS, 80:6351–6355 (Oct. 1983).
Oi et al, PNAS, 80:825–829 (1983).
Olden et al, Biochim Biophys Acta, 650:209–232 (1982).
Ostrowski et al., Mol Cell Biol, 3:2045–2057 (Nov. 1983).
Padmanabhan et al, Endocrinol, 121:1089–1098 (1987).
Parsons et al, Methods Enzymol, 109:736–749 (1985).
Pater et al, Virology, 117:536–540 (1982).
Patillo, Science, :1467–1469 (Mar. 29, 1968).
Patillo et al, Cancer Res, 28:1231–1236 (1968).
Paul et al, Adv Exp Med Biol, 158:89–92 (1982).
Pavlakis et al, PNAS, 80:397–401 (1983).
Peckman et al., Endo, 98:1061–1064 (1976).
Peters et al, J Biol Chem, 259:15123–15130 (Dec. 25, 1984).
Peterson, Meth Enzymol, 91:95–119 (1983).
Pfister et al, Virology, 115:414–418 (1981).
Picard et al, PNAS, 80:417–421 (1983).
Pierce et al, Ann Rev Biochem, 50:465–495 (1981).
Pintel et al, J Virol, 52:320–327 (1984).
Porath, Methods Enzymol, 34:13–30 (1974).
Porath et al., J Chromat, 103:49–62 (1975).
Potter et al, PNAS, 81:7161–7165 (1984).
Prives et al, J Biol Chem, 258:1775–1780 (1983).
Pyati et al, PNAS, 77;3425–3439 (1980).
Racantello et al, Science, 214:916–919 (1981).
Ramabhadran et al., PNAS, 81:6701–6705 (Nov. 1984).
Ramachandran, Gonadotropic Hormones, Li et al Academic Press Inc. 81–91 (1983).
Reddy et al, PNAS, 779:2064 (1982).
Reddy et al, PNAS, 82:3644–3648 (1985).
Reddy et al, Science, 200:494–502 (1978).
Rice et al., PNAS, 79:7862–7865 (Nov. 1982).
Rigby et al, J Gen Virol, 64:255–266 (1983).
Ringold et al., J. Mol. Appl Genet., 1:165–175 (1981).
Rose et al, Cell, 30:753–762 (1982).
Rosemberg et al, J Clin Endocrinol & Metab, 21:1063–1067 (1961).
Rosemberg et al., J Clin Endo Metab, 24:714–728 (1964).
Rosemberg et al, J Clin Endocrinol & Metab, 28:1214–1219 (1968).
Rosen et al, New Eng J Med, 290:1441–1447 (1974).
Ruddon et al, Cancer Res, 39:3885–3892 (1979).
Ruddon et al, Cancer Res, 40:4519–4523 (1980).
Ruohonem–Lehto et al, J. Biotechnology, 6:91–105 (1987).
Ryan, Acta Endocrinol, Suppl. 12:300–323 (1969).
Sairam, Archives Biochem Biophys, 204:199–206 (1980).
Sairam et al, Biochem Biophys Res comm, 48:530–537 (1972).
Sairam et al, Biochem J, 197;541–552 (1981).
Sairam et al, Can J Biochem, 55:755–760 (1977).
Sairam et al., J. Biol. Chem., 258:445–449 (Jan. 10, 1983).
Sairam et al, Science, 229:65–67 (Jul. 5, 1985).
Sambrook et al, Molecular Cloning: A Laboratory Manual, 16.23–16.26 (1989).
Sambrook et al, Molecular Cloning: A Laboratory Manual, 11.2–11.61 (1989).
Sambrook, J. et al., EMBO J, 4:91–103 (1985).
Sarver, Mol. and Cell Biol., 1:486–496 (1981).
Sarver et al., PNAS, 79:7147–7151 (Dec. 1982).
Scahill et al., PNAS, 80:4654–58 (Aug. 1983).
Scheele et al, J Biol Chem, 257:12277–12282(1982).
Schwarzbauer et al, PNAS, 84:754–758 (1987).
Sege et al, Nature, 307:742–745 (Feb. 23, 1984).

Seibel et al, Fertility and Sterility, 43:703–708 (May 1985).
Sekiguchi et al, Gene, 21:267–272 (1983).
Shome et al., J Clin Endocrinol Metab, 39:203–205 (1974).
Shownkeen et al., J Endocrinol, 69:263–273 (1976).
Siddiqui et al, Devel Biol Stand, 54:119–123 (1983).
Sidman, J Biol Chem, 256:9374–9376 (1981).
Skoultchi et al, Symp Giovanni Lorenzini Found., 5:403–412 (1980).
Smith et al, Mol Cell Biol, 3:2156–2165 (Dec. 1983).
Smith et al, Nature, 302:490–495 (Apr. 7, 1983).
Southern et al, J Mol Appl Genet, 1:327–341 (1982).
Stafford et al, Nature, 306:77–79 (Nov. 3, 1983).
Staneloni et al, CRC Crit Rev Biochem, 12:289–326 (Apr. 1982).
Steelman et al, Endocrinol, 53:604–616 (1953).
Stenlund et al., EMBO J., 2:669–673 (1983).
Stenlund et al, J Virol, 48:370–376 (1983).
Stephens et al, Biochem. J., 248:1–11 (1987).
Stevens et al, Nature, 239:143 (1972).
Stewart et al, J Reprod Fert Suppl, 35:1–8 (1987).
Storring et al, J Endocrinol, 91:353–362 (1981).
Stratowa et al, EMBO J, 1:1573–1578 (1982).
Strickland et al, Endocrinol, 110:198A (1982).
Strickland et al., J Biol Chem, 258:5927–5932 (May 10, 1983).
Strickland et al., J Cell Biochem, 29:225–237 (1985).
Subramani et al, Anal Biochem, 135:1–15 (1983).
Subramani et al, Mol Cell Biol. 2:854–864 (Sep. 1981).
Sveda et al, PNAS, 78:5488–5492 (Sep. 1981).
Tashijian et al, PNAS, 70:1419–1422 (1973).
Tojo et al, Endocrinol Japon, 22:585–589 (1975).
Ullrich et al., EMBO J, 3:361–364 (1984).
Ullrich et al., Nature, 309:418–425 (1984).
Urlaub et al., Proc Natl Acad Sci USA, 77:4216–4220 (Jul. 1980).
Valenzuela et al, Nature, 298:347–350 (Jul. 22, 1982).
Valerio et al, Gene, 31:147–153 (1984).
Valle et al, Nature, 291:338–340 (May 28, 1981).
Vamvakopoulos et al, PNAS, 77:3149–3153 (1980).
Van Damme et al, Acta Endocrinol, 91:224–237 (1979).
Van Hell et al, Acta Endocrinologica, 47:409–418 (1964).
Vehar et al, Bio/Technology, 2:1051–1057 (Dec. 1984).
Wagh et al, CRC Crit Rev Biochem, 10:307–377 (1981).
Waldenstrom et al., Gene, 120:175–181 (1992).
Wallace et al., Methods in Enzymology, 152:432–447 (1987).
Wang, Mol. and Cell Biol., 3:1032–1039 (1983).
Warren et al, Cell, 39:547 (1984).
Weintraub et al, Endocr, 112:1331–1345 (1983).
Weintraub et al, Endocrinol, 101:225–235 (1977).
Weintraub et al, J Clin Invest, 52:3135–3142 (1973).
Weintraub et al., J. Biol. Chem., 255:5715–5723 (Jun. 25, 1980).
White et al, Nature, 300:658–659 (Dec. 16, 1982).
White et al, Quart Rev Biophys, 16:151–195 (1983).
Winnacker, Ernst L., From Genes to Clones, 361–363 (1987).
Wood et al, Fertility and Sterility, 43:245–250 (Feb. 1985).
Wood et al, Nature, 312:330–336 (1984).
Yokota et al, PNAS, 81:1070–1074 (Feb. 1984).
Zinn, PNAS, 79:4897–4901 (Aug. 1982).

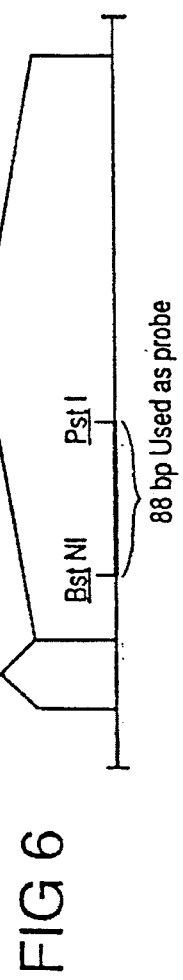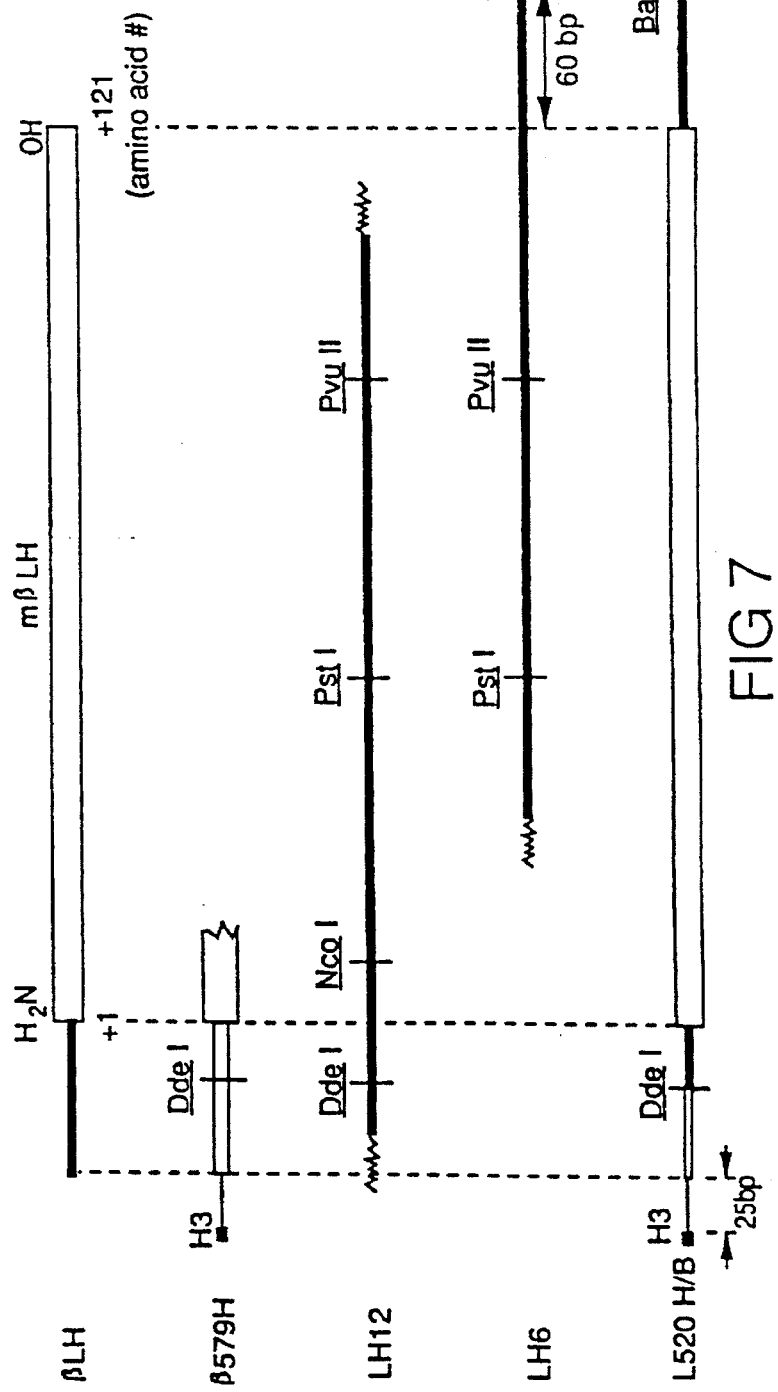
FIG 6
FIG 7

RECOMBINANT HETERODIMERIC HUMAN FERTILITY HORMONES, AND METHODS, CELLS, VECTORS AND DNA FOR THE PRODUCTION THEREOF

CROSS-REFERENCE TO RELATED APPLICATIONS

The present application is a continuation of application Ser. No. 07/515,481, filed Apr. 27, 1990, now abandoned, which application is a continuation-in-part of both Ser. No. 07/323,772, filed Mar. 15, 1989, now abandoned, and Ser. No. 06/696,647, filed Jan. 30, 1985, now U.S. Pat. No. 4,923,805, the entire contents of both of which are hereby incorporated herein by reference. Ser. No. 07/323,772 is a continuation of Ser. No. 06/548,228, filed Nov. 2, 1983 now U.S. Pat. No. 4,840,896. Ser. No. 06/696,647 is a continuation-in-part of said Ser. No. 06/548,228.

BACKGROUND OF THE INVENTION

The present invention relates to the use of recombinant DNA techniques to produce heterodimeric human fertility hormones.

Various polypeptide chains have been expressed, via recombinant DNA technology, in host cells such as bacteria, yeast, and cultured mammalian cells. Fiddes, J. C. and Goodman, H. M. *Nature*, vol. 281, pp. 351–356 (1979) and Fiddes, J. C. and Goodman, H. M., *Nature*, vol. 286, pp. 684–687 (1980) describe the cloning of, respectively, the alpha and beta subunits of human choriogonadotropin (hCG).

Sugimoto U.S. Pat. Nos. 4,383,034, 4,383,035 and 4,383,036 describe processes for producing FSH, LH and hCG, respectively, in which human lymphoblastoid cells are implanted into a laboratory animal, harvested from the animal, and cultured in vitro; accumulated hormone is then harvested from the culture. This technique is not capable of producing substantially pure hormone free of any other human fertility hormone.

Cohen et al, U.S. Pat. No. 4,468,464 mentions the production of fertility hormones by recombinant DNA techniques. However, Cohen et al only uses a prokaryotic system which cannot produce biologically active human fertility hormone.

Pierce et al, *Ann. Rev. Biochem.*, 50, 465–95 (1981) states that the alpha and beta subunits of LH are known to associate in vitro. The subunits referred to in this paper are obtained by dissociating naturally occurring dimeric hormone and allowing the units to reassociate. Such a disclosure does not permit the prediction that when synthesized by non-specialized cells transformed with recombinant DNA, the subunits would be properly glycosylated and folded for association so as to produce a biologically active hormone.

While many human proteins have been produced by recombinant DNA techniques the production of biologically active heterodimeric hormones by such techniques has not heretofore been accomplished. Heterodimeric fertility hormones are produced in the human body by highly specialized, differentiated cells which have evolved over a long period of time to carry out the specialized function of producing each particular hormone. The mechanism by which post-translational heterodimeric assembly occurs intracellularly in these differentiated cells is not known, but it is known that proper assembly is necessary for biological activity. Undifferentiated cells do not, as far as is known, normally produce hormones. Thus, whether or not a biologically active heterodimeric hormone could be produced in undifferentiated cells transformed with DNA encoding the alpha and beta subunits was totally unpredictable.

SUMMARY OF THE INVENTION

The present invention stems from the unpredictable discovery that biologically active heterodimeric human fertility hormones can be produced in eukaryotic cells transformed by vectors containing the alpha and beta subunits of the hormone controlled by separate promoters. While alpha and beta subunits produced in separate cultures will not reassociate to form biologically active hormones, it has unexpectedly been discovered that when both subunits are produced in the same cell, a hormone is expressed which is biologically active.

Thus, the present invention includes the substantially pure heterodimeric human fertility hormones which can now be made totally free of other fertility hormones as well as any other human proteins. It also includes the process for production of such hormones, eukaryotic cells which have been transformed to so produce the hormones and vectors containing the DNA of both the alpha and beta subunits.

The present invention also includes the DNA encoding the beta subunits of hLH and hFSH, including cDNA coding for the beta subunit of human FSH, expression vectors containing such DNA and cells transfected therewith. The invention also includes DNA derivatives according to the genetic code which on expression code for the beta subunit of human FSH according to the present invention. The polypeptide structure of the beta subunit of hFSH has never before been accurately set forth.

Thus, in general, the present invention features, in one aspect, a substantially pure heterodimeric human fertility hormone composed of two different subunits and the process for the production thereof by means of which the two subunits are synthesized by single cell line, each cell having been transformed by an expression vector containing heterologous DNA encoding both subunits under control of separate promoters or two expression vectors each containing heterologous DNA encoding the separate subunits. The cell line is composed of eukaryotic cells which permit appropriate post-translational modification of the subunits such that the formed protein is biologically active. Because of the recombinant DNA technique which is used, the hormones produced are substantially pure and free of any other fertility hormones or any other human proteins. The preferred fertility hormones which are produced in accordance with the present invention are hCG, luteinizing hormone (LH) and follicle stimulating hormone (FSH).

In another aspect, the present invention features a cell transformed by at least one expression vector, which cell is capable of producing a biologically active heterodimeric protein that is encoded at least in part by the vector. In preferred embodiments: a second expression vector encodes a second portion of the protein or at least two subunits of the protein are encoded by a single expression vector; the vectors are autonomously replicating, preferably a replicating virus or a plasmid; the cell is a mammalian cell, such as a monkey or mouse cell; transcription of the different subunits is under the control of the SV40 late promoter; transcription of the alpha subunit of the protein is under the control of the SV40 early promoter and transcription of the beta subunit is under control of the mouse metallothionein promoter, or transcription of both subunits is under the control of the mouse metallothionein promoter; and the expression vector which includes the mouse metallothionein promoter also includes at least the 69% transforming region of the bovine papilloma virus (BPV) genome.

In another aspect, the invention features an autonomously replicating expression vector including two genes encoding two different heterologous proteins, the genes being under the control of two different promoters, most preferably a metallothionein promoter and a BPV promoter; the use of different promoters advantageously minimizes the possibility of deleterious recombinations.

In a further aspect, the invention features the DNA for the beta subunits of hLH and hFSH.

As used herein, "subunit" refers to a portion of a protein, which portion, or homologue or analogue thereof, is encoded in nature by a distinct mRNA. Thus, for example, a heavy chain and a light chain of an IgG immunoglobulin are each considered a subunit. Insulin, on the other hand, is composed of two chains which are not considered subunits, because both are, in nature, encoded by a single mRNA, and cleavage into two chains naturally occurs only after translation.

The term "expression vector" refers to a cloning vector which includes heterologous (to the vector) DNA under the control of control sequences which permit expression in a host cell. Such vectors include replicating viruses, plasmids, and phages. Preferred vectors are those containing at least the 69% transforming region, and most preferably all, of the bovine papilloma virus genome.

The invention permits the production of a biologically active heterodimeric human fertility hormone from a single culture of transformed cells which hormone undergoes, in the culture, post-translational modification, e.g. glycosylation and proteolytic processing, for biological activity and stability.

In preferred embodiments, each expression vector is autonomously replicating, i.e., not integrated into the chromosome of the host cell. The use of autonomously replicating expression vectors prevents undesirable influence of the desired coding regions by control sequences in the host chromosome.

Other advantages and features of the invention will be apparent from the following description of the preferred embodiments thereof, and from the claims.

BRIEF DESCRIPTION OF THE DRAWINGS

We turn now to the preferred embodiments of the invention, first briefly describing the drawings thereof.

FIG. 6 is a diagram illustrating the location of an 88 bp probe within the beta hCG cDNA clone.

FIG. 7 illustrates the beta LH restriction map, and the pieces used in the construction shown in FIG. 8.

DETAILED DESCRIPTION OF PREFERRED EMBODIMENT

The cloning vectors of the invention have the general structure recited in the Summary of the Invention, above. Preferred vectors have the structures shown in the Figures, and are described in more detail below.

Construction of Cloning Vectors

Isolation of cDNA Clones Encoding the Alpha and Beta Subunits of hCG

All of the techniques used herein are described in detail in Maniatis et al, (1982) *Molecular Cloning: A Laboratory Manual* (Cold Spring Harbor Laboratory), hereby incorporated by reference.

RNA is extracted from placental tissue by the following method. Homogenization of the tissue is carried out in a 1:1 mixture of phenol:100 mM Na-acetate (pH 5.5) containing 1 mM EDTA, that has been warmed to 60° C. for 20 min. After cooling on ice for 10 min., the phases are separated by centrifugation. The hot phenol extraction is repeated twice more followed by two extractions with chloroform.

RNA is precipitated from the final aqueous phase by the addition of 2.5 volumes of ethanol.

In order to enrich for poly $A^+$ mRNA, placental RNA is passed over oligo (dT)-cellulose in 0.5M NaCl buffered with 10 mM Tris-HCl, pH 7.5, and washed with the same solution. Poly $A^+$ mRNA is eluted with 10 mM Tris-HCl (pH 7.5), 1 mM EDTA, 0.05% SDS and precipitated twice with ethanol. Typical initial yields are 1.5–2.0 mg of total RNA per g of tissue, of which about 2% is poly $A^+$ mRNA.

Placental cDNA libraries are constructed by reverse transcription of placental mRNA, second strand synthesis using E. coli DNA polymerase I (large fragment), treatment with S1 nuclease, and homopolymer tailing (dC) with terminal deoxynucleotidyl transferase; all such procedures are by conventional techniques.

In a typical preparation, 20–30% conversion of mRNA to single strand (ss) cDNA; 70% resistance to digestion with nuclease S1 after second strand synthesis; and dC "tails" of ten to twenty-five bases in length, are obtained. These cDNA molecules are then annealed to DNA fragments of the plasmid pBR322, which has been digested with PstI, and to which dG "tails" have been added. These recombinant plasmids are then used to transform *E. coli* cells to generate a cDNA library (transformed cells are selected on the basis of tetracycline resistance).

In order to identify the human alpha hCG clone, a 219 bp fragment of a mouse alpha thyroid stimulating hormone (TSH) clone is used as a hybridization probe. This probe has 77% sequence homology with the human clone. It is radioactively labeled by nick translation and hybridized to the cDNA library under conditions that take into account the extent of homology. Strongly hybridizing clones are analysed by restriction mapping and clones containing the complete coding sequence of alpha hCG are verified by DNA sequencing.

Construction of Plasmid p alpha SVHVP1

Figure 1:
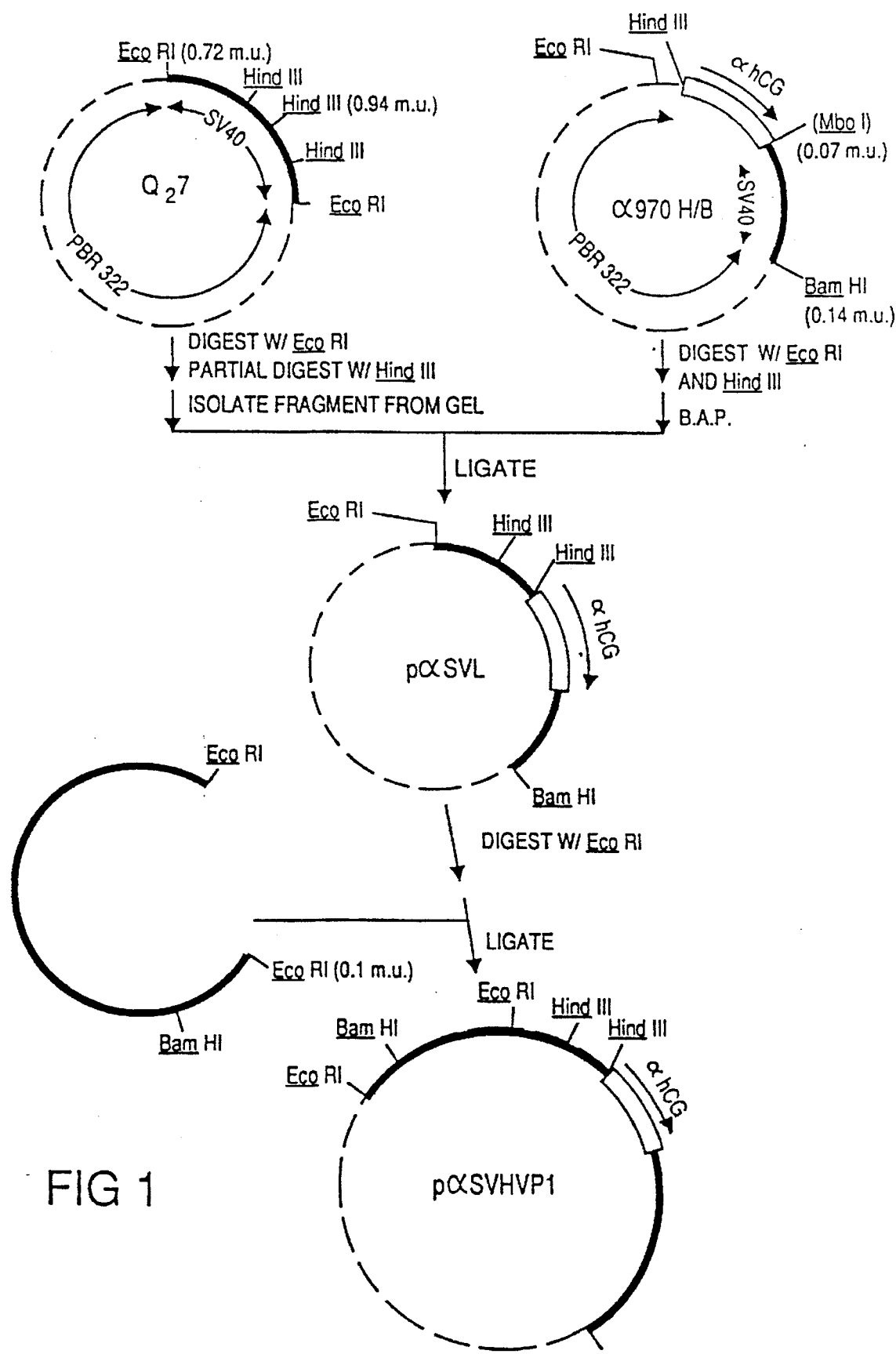
FIG. 1 is a diagrammatic illustration of the construction of the plasmid p alpha SVHVP1, which contains the alpha hCG cDNA clone, portions of SV40 viral DNA, and sequences of the plasmid pBR322.

Referring to FIG. 1, in order to construct the plasmid alpha 970 H/B, a cDNA clone containing the alpha hCG fragment is digested with NcoI. The NcoI site, just 5' to the ATG codon signalling initiation of translation, is filled in and ligated to a synthetic HindIII linker. Similarly, the natural HindIII site in the 3' untranslated region of the clone is cut, filled in with *E. coli* DNA polymerase Klenow, and then ligated to a synthetic BamHI linker. This fragment is cloned into the plasmid pBR322 between its HindIII and BamHI sites to generate the plasmid alpha 574 H/B. This plasmid is digested with BamHI, treated with alkaline phosphatase, and ligated to the 396 bp Sau3A fragment of SV40 DNA (from 0.07 to 0.14 map units) which has been isolated from a polyacrylamide gel. The ligation mix is used to transform *E. coli* to ampicillin resistance and the desired plasmid, alpha 970 H/B, is identified among the transformants.

The plasmid $Q_27$ is constructed by cutting SV40 at its HsaII site, making flush ends by digestion with nuclease S1, ligating on EcoRI linkers, digesting with EcoRI, and cloning the resulting 1436 bp fragment into the EcoRI site of pBR322.

Referring to FIG. 1, $Q_27$ is digested completely with EcoRI and partially with HindIII; the fragment from 0.72 to 0.94 map units is isolated and cloned into alpha 970 H/B, which has been digested with ScoRI and HindIII and treated with alkaline phosphatase. The ligation mix is used to transform *E. coli*, and the desired plasmid, p alpha SVL, is identified among the transformants by restriction mapping.

p alpha SVL is digested with EcoRI and the fragment of SV40, with EcoRI ends, extending from 0 to 0.72 map units, and containing the SV40 origin of replication and the intact early region, is ligated to it to generate the plasmid p alpha SVHVP1, which is isolated from *E. coli* transformants.

Construction of Plasmid p beta SVVP1

Figure 2:
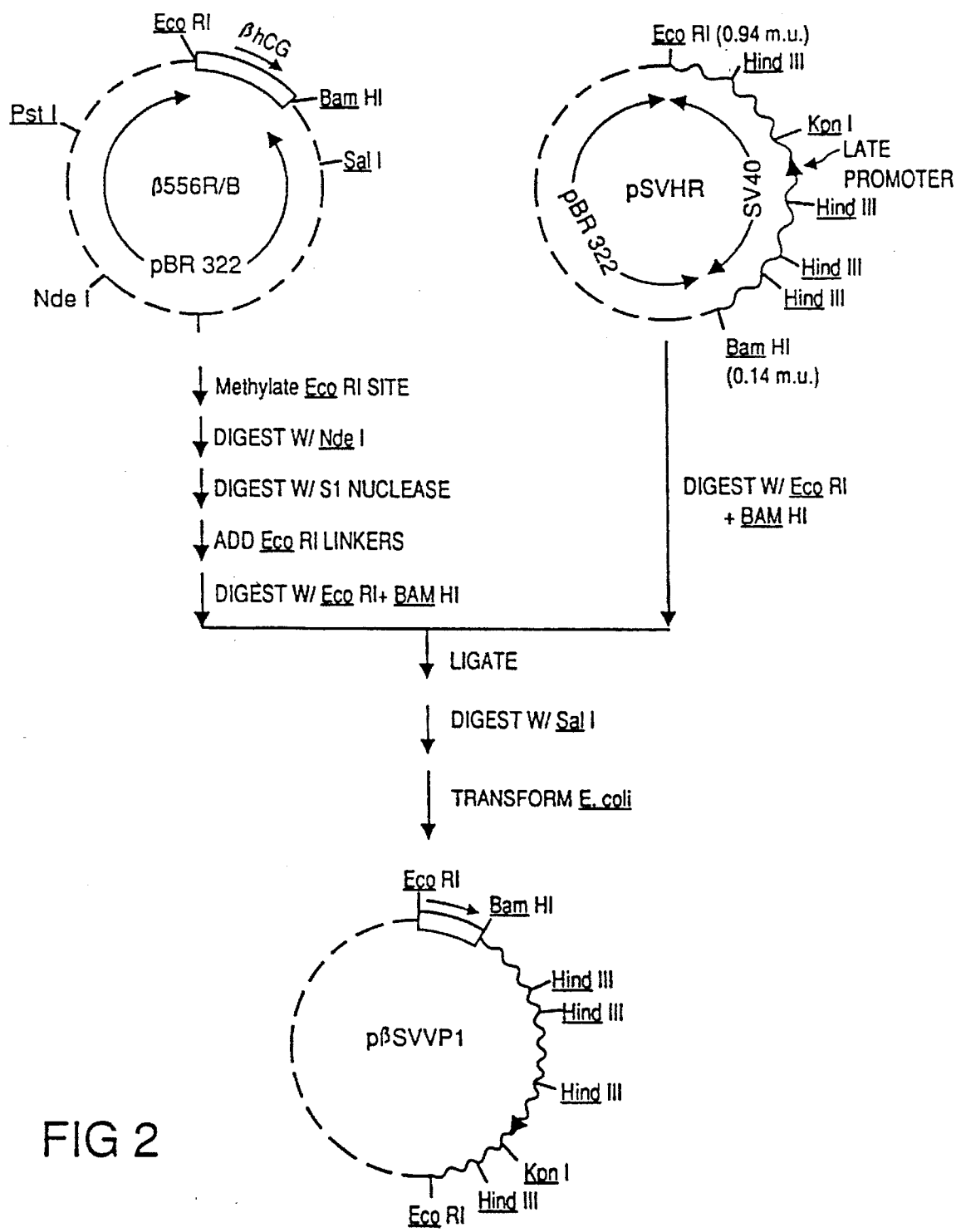
FIG. 2 is a diagrammatic illustration of the construction of plasmid p beta SVVP1, which incorporates the beta hCG cDNA clone, regions of SV40 DNA and a portion of pBR322 including the region conferring resistance to ampicillin on host E. coli.

A 579 bp cDNA clone coding for beta hCG was obtained from John C. Fiddes at Cold Spring Harbor Laboratory, Cold Spring Harbor, New York (Fiddes et al, *Nature*, vol. 286, pp. 684–687 (1980)). This fragment is ligated at each end to synthetic BamHI linkers. After digestion by HgaI restriction enzyme, the ends are filled in with Klenow DNA polymerase and synthetic EcoRI linkers are ligated on so that an EcoRI site is about 10 bp 5' to the ATG codon of the signal peptide coding sequence. A BamHI site is about 60 bp 3' to the nonsense codon marking the end of the coding sequence. Referring to FIG. 2, this 556 bp EcoRI-BamHI fragment is isolated and cloned into pBR322, between the EcoRI and BamHI sites, to give the plasmid p beta 556 R/B.

In order to construct the plasmid pSVHR (FIG. 2), SV40 DNA is partially digested with HindIII to yield linear molecules, digested with nuclease S1 to make flush ends, ligated to synthetic EcoRI linkers and digested with EcoRI and BamHI. The fragment from 0.94 to 0.14 map units, containing the SV40 origin of replication and early region, is cloned into pBR322 as an EcoRI-BamHI piece.

Referring still to FIG. 2, the EcoRI site of the plasmid p beta 556 R/B is methylated in a reaction catalyzed by EcoRI methylase, following which the plasmid is cut with NdeI. EcoRI linkers are ligated to the S1 treated NdeI flush ends and activated by digestion with EcoRI, which is followed by digestion with BamHI.

The SV40 fragment of pSVHR from the EcoRI site to the BamHI site is isolated and ligated in a reaction mix containing the digestion fragments of p beta 556 R/B. Following ligation, the mix is digested with SalI to eliminate plasmids which have re-inserted the EcoRI (NdeI) to BamHI piece of pBR322. *E. coli* is transformed with the digested ligation mix and p beta SVVP1 is identified and isolated.

Construction of the Plasmid p Alpha Beta SVVP1

Figure 3:
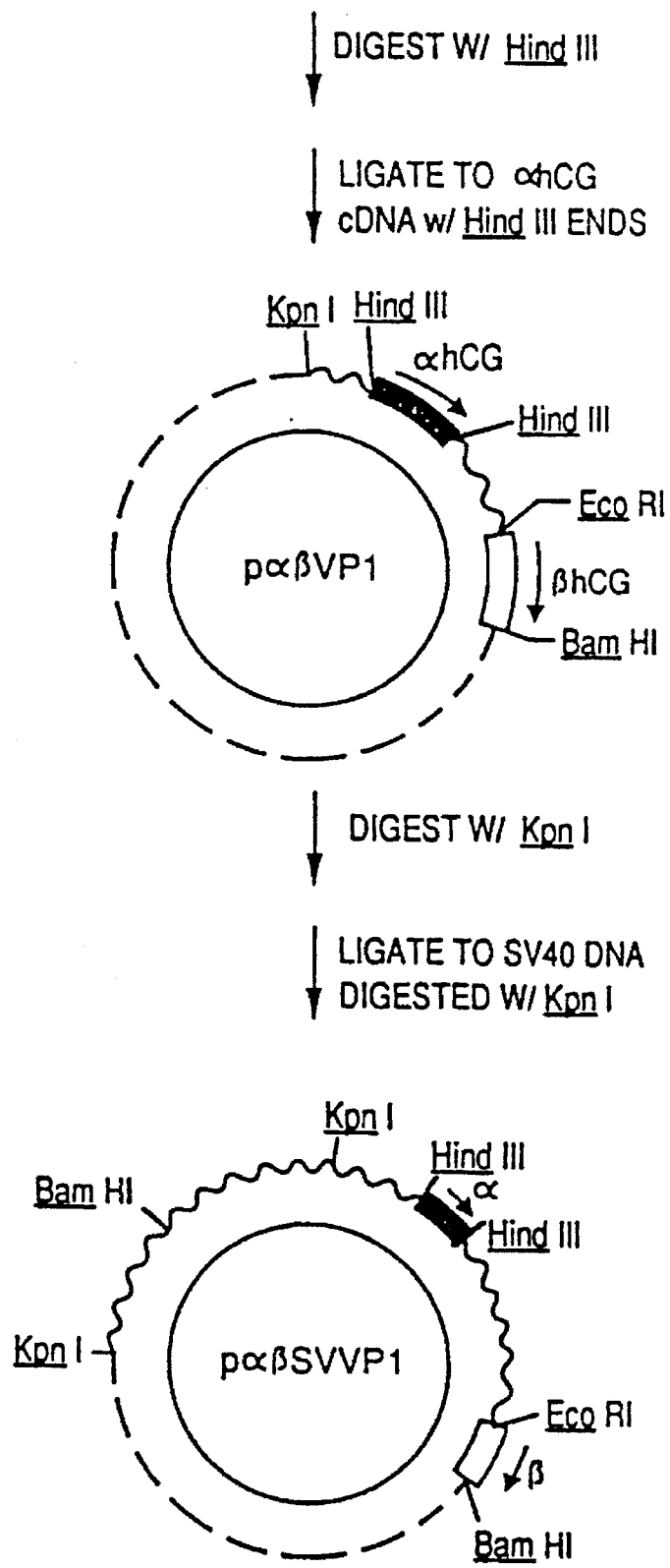
FIG. 3 is a diagrammatic illustration of the construction of the plasmid p alpha beta SVVP1 in which the alpha and beta hCG cDNA clones are inserted into SV40 DNA.
Figure 3:
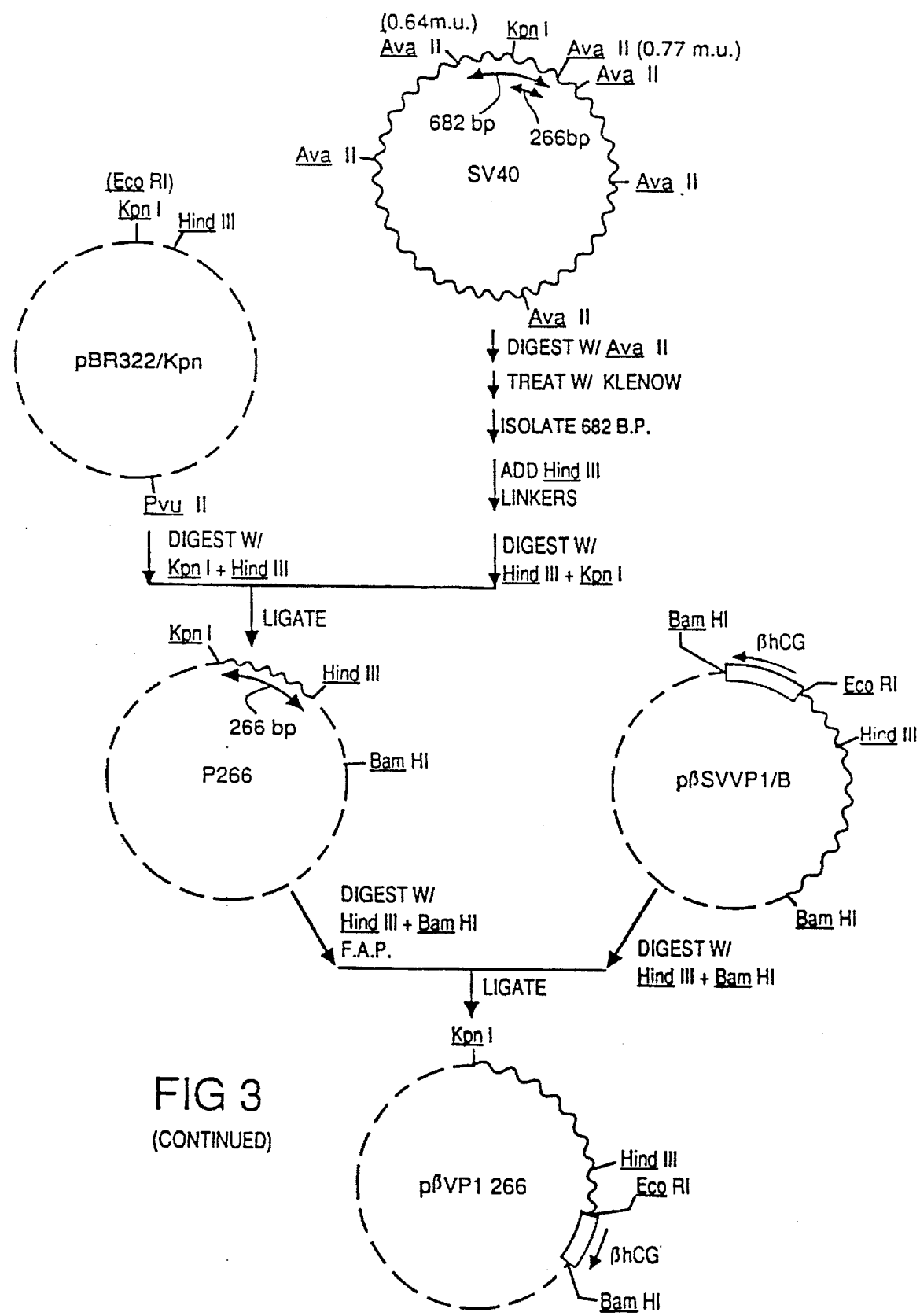

Referring to FIG. 3, pBR322/Kpn is derived from pBR322 by inserting a KpnI linker into its unique EcoRI site, after this site is deleted by digestion with EcoRI, followed by digestion with S1 nuclease.

Referring still to FIG. 3, SV40 DNA is digested with AvaII. The staggered ends of the resulting fragments are filled in by Klenow DNA polymerase to form flush ends, and the mixture is then fractionated on a polyacrylamide gel. The 682 base pair fragment (0.64 to 0.77 map units) containing the origin of replication and to the unique KpnI site is isolated from the gel, ligated to synthetic HindIII linkers, and digested with HindIII and KsnI.

The resulting fragments are ligated to pBR322/Kpn. p266, which contains the 266 base pair KpnI HindIII fragment, including the SV40 late promoter region, is isolated. p266 is cut with HindIII and BamHI, and treated with bacterial alkaline phosphatase.

Still referring to FIG. 3, p beta SVVPI/B is constructed as follows: p beta SVVPI (FIG. 2) is cut with EcoRI, followed by ligation to eliminate pBR322 sequences. Subsequently, this DNA is cut with BamHI and cloned into the BamHI site of pBR322.

The resulting plasmid, p beta SVVPI/B, is then digested with HindIII and BamHI and the 1003 base pair HindIII-BamHI fragment is ligated into p266 to yield the plasmid p beta VP1 266, in which the beta hCG cDNA is positioned downstream from the SV40 late promoter in such a way that its RNA transcript would be spliced as if it were the viral VP1 transcript.

The alpha hCG cDNA is inserted into p beta VP1 266 as a HindIII fragment, which has been cut at its HindIII site and treated with bacterial alkaline phosphatase. *E. coli* transformants derived from this ligation are screened by restriction mapping, and plasmids are isolated that have the desired structure, in which the alpha hCG cDNA has replaced VP2 in the correct orientation, followed downstream by the beta hCG cDNA, which has replaced VP1.

One such isolated plasmid, p alpha beta VP1, is used to complete the construction of p alpha beta SVVP1. The plasmid is cut with KpnI, and the full SV40 genome, cut with KpnI, is inserted by ligation into this site. Following transformation of *E. coli*, a plasmid with the required structure, p alpha beta SVVP1, is isolated. This plasmid contains DNA encoding both the alpha and beta subunits of hCG, and thus is capable of directing the expression, in host mammalian cells, of both subunits, whereby biologically functional, glycosylated heterodimeric hCG is produced (glycosylation occurs post-translationally).

Construction of Plasmids pRF 375 and pRF 398

Figure 4:
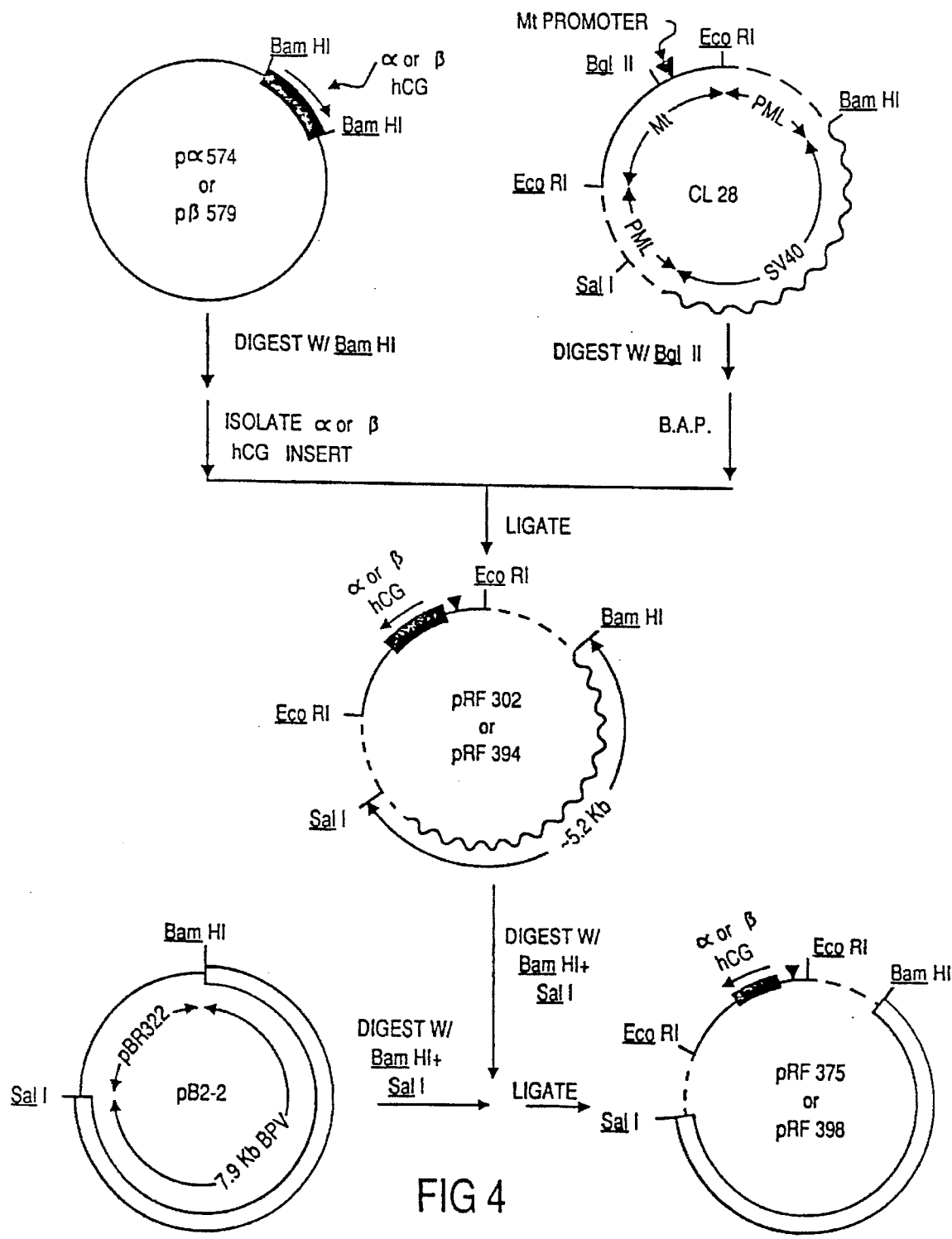
FIG. 4 is a diagrammatic illustration of the construction of the plasmids pRF375 and pRF398.

Referring to FIG. 4, the plasmid CL28 (identical to plasmid JYMMT(E); Haner et al., *J. Mol. Applied Gen.*, 1, 273–288 (1983)), containing the murine metallothionein promoter, SV40 DNA, and pBR322 sequences, is cut with the restriction endonuclease Bgl II. At this site are inserted cDNA clones of either alpha hCG or beta hCG, containing untranslated regions of about 10 and 30 bp at their 5' and of about 220 and 60 bp at their 3' ends. These clones have been genetically engineered by the addition of synthetic BamHI linkers at their termini.

The resulting plasmids pRF 302 (alpha) or pRF 394 (beta) are digested with restriction enzymes BamHI and SalI to release the SV40 DNA sequences.

Plasmid pB2-2, which contains the entire BPV genome, and some pBR322 sequences, is digested with BamHI and SalI to yield the BPV genome with BamHI/SalI ends; this fragment is ligated into pRF 302 (alpha) and pRF 394 (beta) containing the metallothionein-hCG sequences.

Following transformation of *E. coli*, plasmids pRF 375 and pRF 398 are identified and isolated. They encode alpha hCG or beta hCG, respectively, under the control of the mouse metallothionein promoter.

Construction of the Plasmid RF 398 alpha $t_2$

Figure 5:
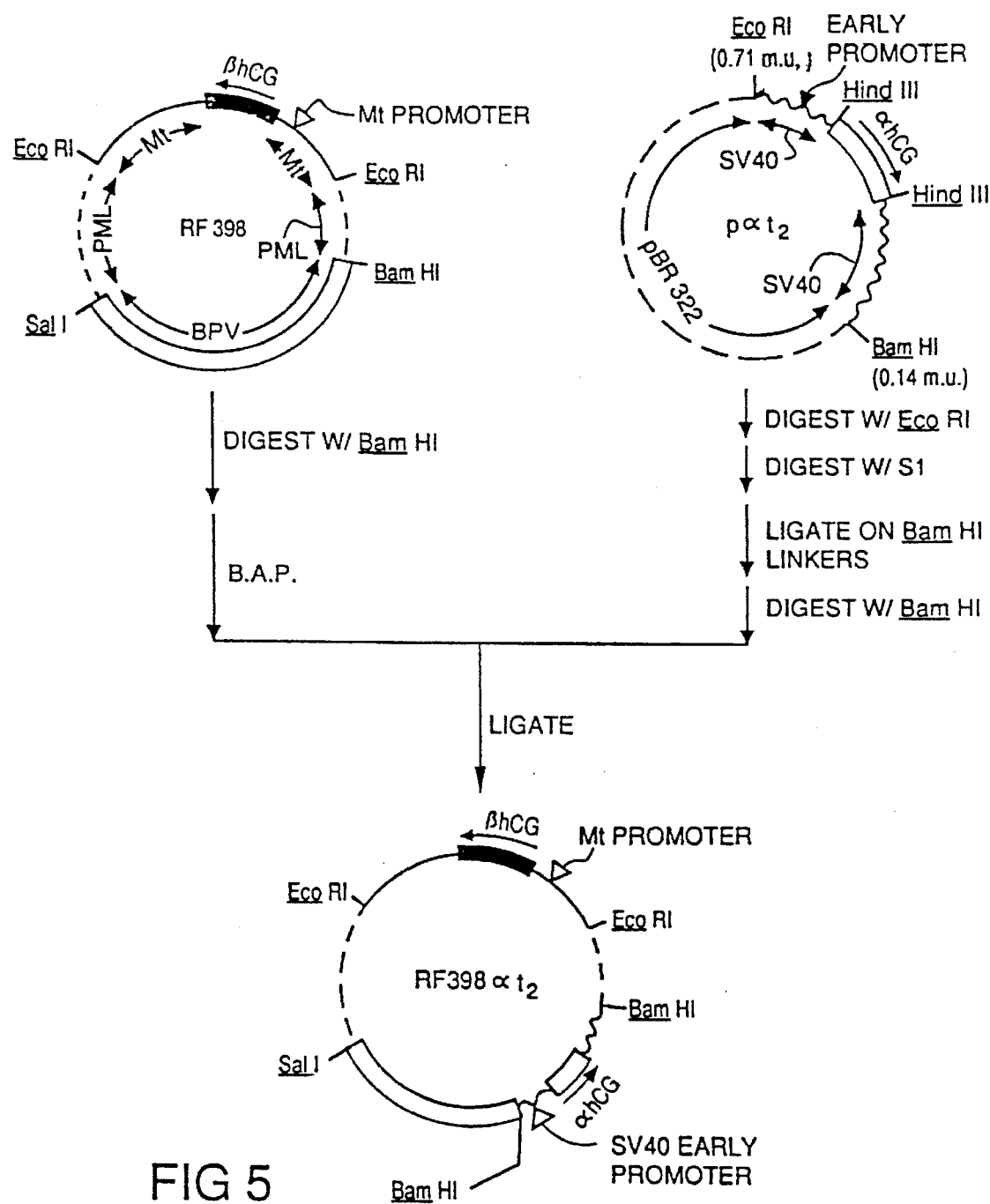
FIG. 5 is a diagrammatic illustration of the construction of the plasmid RF398 alpha $t_2$.

Referring to FIG. 5, the plasmid p alpha $t_2$ is derived by cloning the alpha hCG 574 HindIII fragment into plasmid pVBt2 (V. B. Reddy et al., *PNAS*, 79, 2064–2067, 1982). p alpha $t_2$, which contains the alpha hCG cDNA under the control of the SV40 early promoter, is digested with EcoRI. The 5' overhangs are removed by S1 nuclease digestion prior to the addition of synthetic BamHI linkers by blunt end ligation.

Plasmid RF 398 (FIG. 4) is digested with BamHI and treated with bacterial alkaline phosphatase. The 1735 base pair BamHI fragment of p alpha $t_2$ is inserted in to RF 398. The resulting plasmid RF 398 alpha $t_2$ is isolated from *E. coli* transformants. This plasmid thus has the beta hCG cDNA in a transcriptional unit under control of the mouse metallothionein promoter and the alpha hCG cDNA in a transcriptional unit controlled by the SV40 early promoter.

Expression of Luteinizing Hormone (LH) cDNA Clones

Construction of a Human Pituitary cDNA Library

RNA is prepared from human pituitaries by homogenizing 5 to 10 grams of the frozen glands in 20 ml of a solution containing 4M guanidine thiocyanate, 1M 2-mercaptoethanol, 0.05M Na-acetate (pH 5.0), and 0.001M EDTA. One g CsCl is added per ml of homogenate and the suspension is centrifuged at 2,000 rpm for 15 min. The supernatant is layered carefully over a 15 ml cushion of CsCl solution (containing 1.25 ml of 1M Na-acetate (pH 5), 62.5 microliters of 0.4M EDTA and 39.8 g of CsCl in a final volume of 35 ml) and centrifuged at 45,000 rpm in the Ti 70 rotor of a Beckman ultracentrifuge for 18–24 h at 20° C. The RNA visible as a pellicle in the gradient is removed with a syringe, diluted, and precipitated by the addition of two volumes of ethanol. Following three cycles of dissolution and reprecipitation, the RNA pellet is dissolved in $H_2O$ and brought to 0.01M Tris-HCl (pH 7.5) and 0.5M NaCl by the addition of concentrated stock solutions. The preparation is then enriched for poly $A^+$ mRNA by two passes over oligo dT-cellulose, as described above in the case of placental RNA.

A human pituitary cDNA library is constructed from the poly $A^+$ mRNA as described above for placental poly $A^+$ mRNA except that both the large fragment *E. coli* DNA polymerase I and the avian myeloblastosis virus reverse transcriptase are used sequentially for second strand cDNA synthesis. Reverse transcriptase is used first. The reaction is stopped by phenol extraction. The aqueous phase of the centrifuged extract is applied to a 5 ml column of BioGel A-5m. Fractions containing high molecular weight material are pooled, concentrated, precipitated with two volumes of ethanol, dried, and dissolved in 100 mM Tris-HCl (pH 8.3), 10 mM $MgCl_2$, 140 mM KCl, 20 mM 2-mercaptoethanol, 1 mM of each of the four deoxyribonucleoside triphosphates, for reverse transcription. Reverse transcriptase is added to about 20 units per microgram of cDNA. Double stranded cDNA is then treated with nuclease S1, tailed, and cloned as described above.

Isolation of Beta LH cDNA Clones

Colonies grown on nutrient agar plates containing 25 micrograms per ml of tetracycline are transferred to nitrocellulose filters. Colonies are lysed in situ by treatment with 0.5M NaOH and neutralized with 0.5M Tris-HCl (pH 7.4) containing 1.5M NaCl. Liberated DNA is fixed to the filter by baking at 80° C. in a vacuum oven for 2 h. The filters are screened by hybridization to a $^{32}P$ labeled 88 base pair fragment of the beta hCG clone corresponding to amino acids 16 to 45 of the mature hCG beta chain, which has 29 of 30 amino acids in common with this region of the beta LH polypeptide (FIG. 6). Hybridization is carried out overnight at 32° C. in 50% formamide, 0.75M NaCl, 0.075M Na-citrate (pH 7.0), 2.5% dextran sulfate, 0.1% polyvinylpyrollidone, 0.1 mg per ml bovine serum albumin, and at least $10^5$ cpm per filter of $^{32}P$-labeled 88 bp beta hCG fragment. Filters are washed several times in 0.15M NaCl, 0.015M Na-citrate at 37° C. before autoradiography. One of the positive isolated clones LH12 (FIG. 7), is used further. LH12 is 365 bp long and includes sequences coding for 15 amino acids of the pre-beta signal sequence plus 105 amino acids of the mature beta LH polypeptide. Its nucleotide sequence is determined. Since the complete mature beta LH is not coded by LH12, further screening of the human pituitary cDNA library is carried out using a 240 bp NcoI-PvuII fragment of LH12 (FIG. 7) as a $^{32}P$ labeled hybridization probe. The clone LH6 (FIG. 7) is isolated from this screening. LH6 contains the complete 3' end of beta LH, including the region corresponding to the untranslated portion of the mRNA through 27 A residues of the poly A "tail" of the mRNA. No clones are found that extended further than LH12 in the 5' direction. DNA sequencing of the complete, combined mature beta LH coding regions reveals two differences in the amino acid sequence of beta LH from the published protein sequence data: position 42 is a methionine and position 55 is a valine. Also, the mature beta LH contains 121 amino acids, based on the cDNA sequence.

Figure 8:
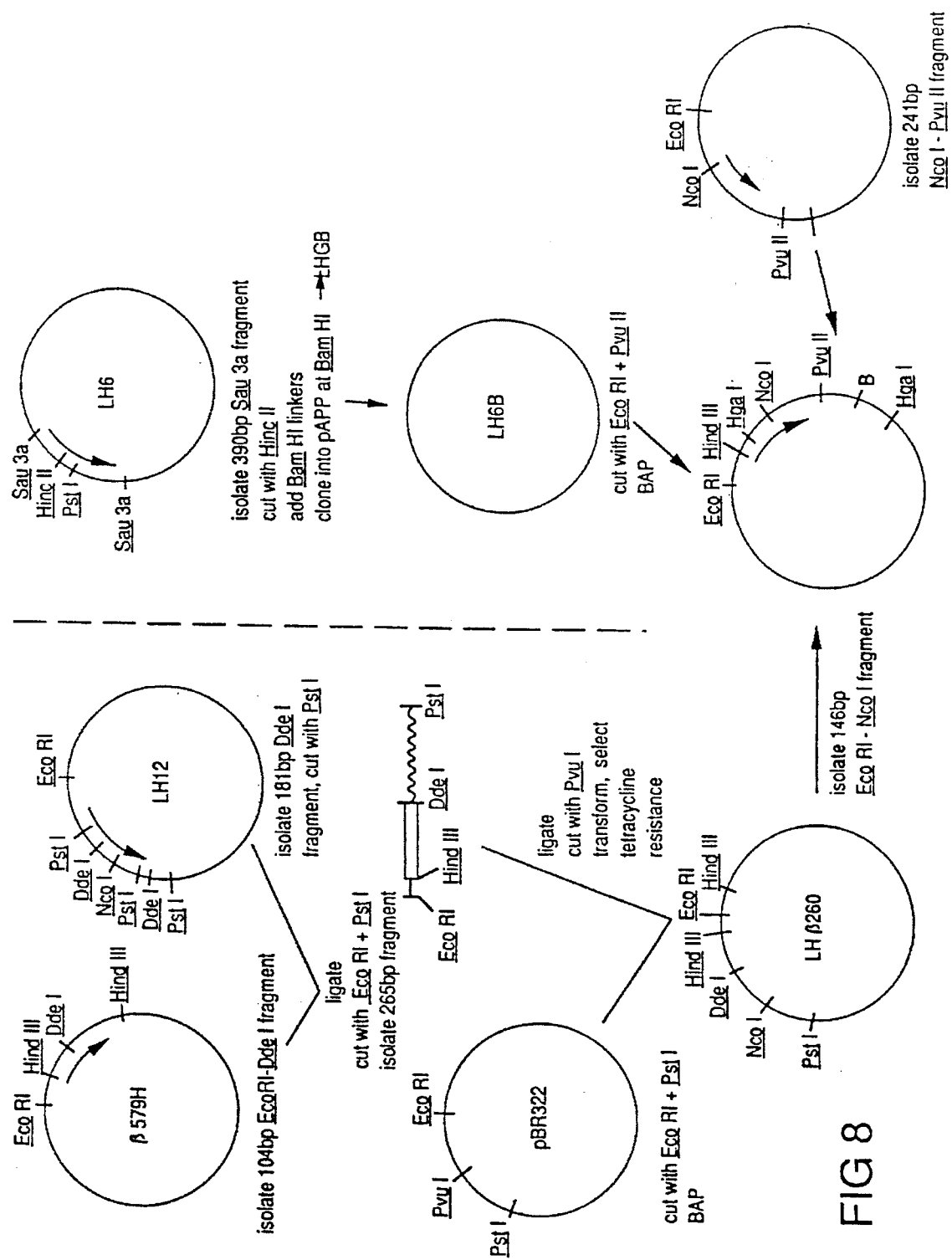
FIG. 8 is a diagrammatic illustration of the construction of a plasmid, LH520H/B, containing the complete mature beta LH cDNA clone.

A clone containing an intact signal peptide coding sequence and the complete mature beta LH sequence is constructed as shown in FIG. 8, using the restriction fragments illustrated in FIG. 7. A 104 bp EcoRI-DdeI fragment is isolated from the plasmid beta 579 H and ligated to an isolated 181 bp DdeI fragment, subsequently digested with PstI, from the LH12 plasmid. Following ligation overnight at 15° C., the ligation mix is digested with EcoRI and PstI and fractionated on a 7% polyacrylamide gel from which the desired 256 bp fragment is isolated. This fragment fuses the beta hCG signal sequence to that of the pre-beta LH in such a way as to provide a coding sequence for a 20 amino acid signal peptide.

The 256 bp EcoRI-PstI fragment is cloned into pBR322 digested with EcoRI and PstI so as to give the plasmid LH beta 260. The 146 bp EcoRI-NcoI fragment indicated in FIG. 8 is isolated from a polyacrylamide gel and used later in the construction as described below.

The LH6 plasmid (FIG. 8) is digested with Sau3a and the 390 bp fragment is isolated by polyacrylamide gel electrophoresis. This fragment is then digested with HincII, ligated to BamHI linkers, digested with BamHI, and cloned into the plasmid pAPP at the BamHI site. pAPP is derived from pBR322 by digestion with AvaI, filling in the 5' overhang with the dNTP's and the large fragment DNA polymerase I of *E. coli*, digestion with PvuII, and ligation to close the plasmid so as to eliminate the PvuII site. The plasmid LH6B, isolated from the ligation of the 340 bp BamHI fragment into the BamHI site of pAPP, is digested with EcoRI and PvuII, and treated with bacterial alkaline phosphatase. The fragments are ligated to a mixture of the 145 bp EcoRI-NcoI fragment of LH beta 260, described above, and the isolated 241 bp NcoI-PvuII fragment from the plasmid LH12 shown in FIG. 8. The ligation mix is used to transform *E. coli* to ampicillin resistance. The plasmid LH 520 H/B is found among the transformants. LH 520 H/B contains a complete beta LH coding sequence including a hybrid signal peptide sequence.

Construction of p Alpha LHSVVP1

In order to express this pre-beta LH clone is an SV40-based vector, as had been done for the pre-alpha and pre-beta hCG clones described previously, it is desirable to place an EcoRI site very close to the ATG of the pre-beta coding sequence. This is accomplished by digesting LH520 H/B with HgaI, filling in the 5' overhang, ligating on synthetic EcoRI linkers, digesting with EcoRI and BamHI, and cloning the isolated 496 bp EcoRI-BamHI fragment into pBR322 digested with EcoRI and BamHI and treated with bacterial alkaline phosphatase. The plasmid pLH496 R/B is isolated from *E. coli* transformed with this ligation mix and is used as the source of the 496 bp fragment to be expressed.

Figure 9:
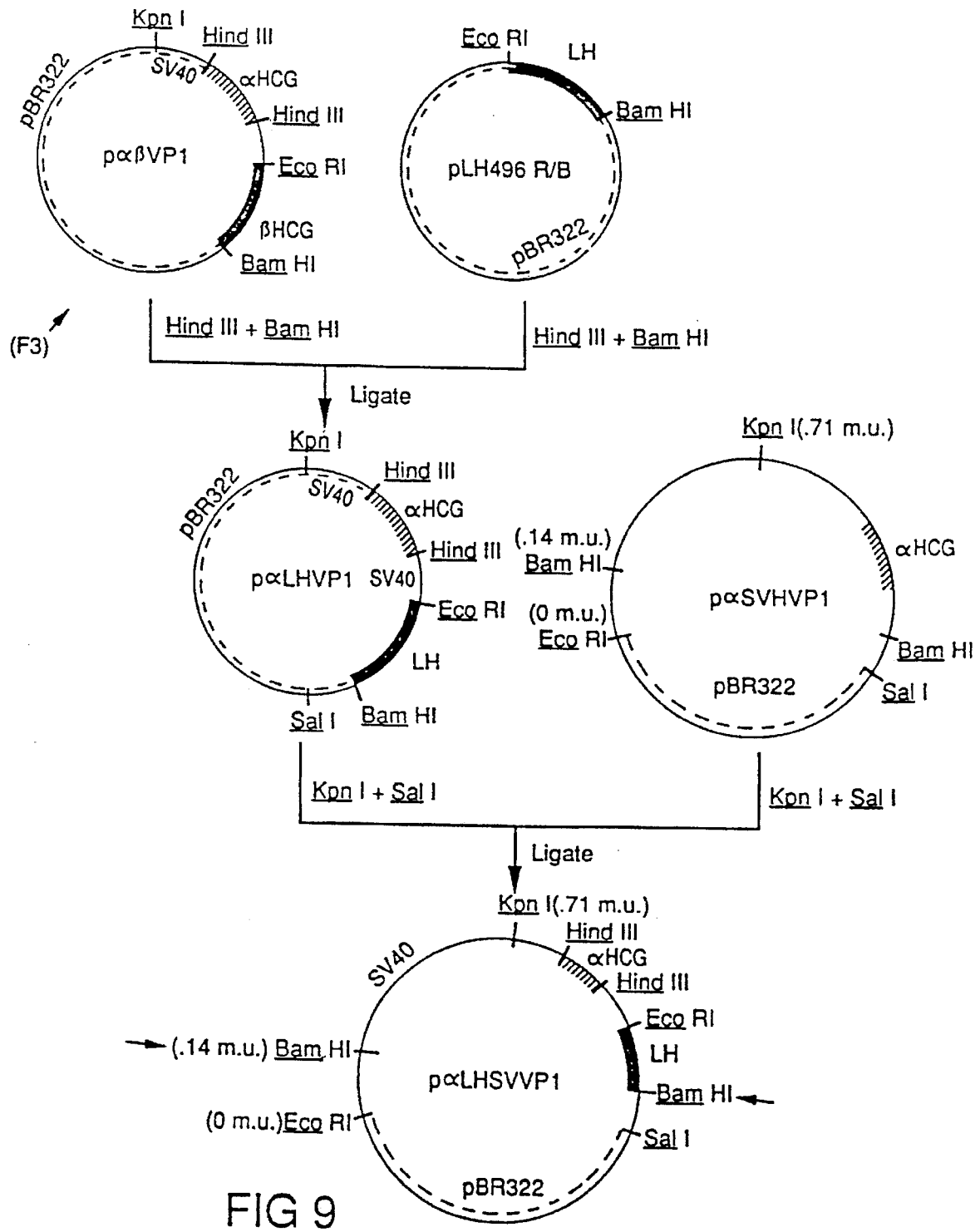
FIG. 9 is a diagrammatic illustration of the construction of the viral vector p alpha LHSVVP1.

The plasmid p alpha beta VP1, whose construction and use in expression both subunits of hCG is described earlier (FIG. 3), is digested with EcoRI and BamHI and ligated in a reaction mix containing the plasmid pLH496 R/B which had been digested with both of these enzymes (FIG. 9). The plasmid p alpha LHVP1 is identified among the *E. coli* transformants. As shown in FIG. 9, the intact SV40 viral early region is taken from p alpha 8VHVP1 (FIG. 1) and inserted by ligation as a KsnI-SalI fragment into p alpha LHVP1 which had been digested with KsnI and SalI to give the plasmid p alpha LHSVVP1. By cutting this plasmid with BamHI and religating, the virus alpha LHSVVP1 is formed. This virus contains cloned cDNA's for the common (to LH and hCG, as well as FSH and TSH) alpha subunit and the specific beta LH subunit under control of the SV40 late promoter. The cloned cDNA's are positioned in such a way that the common alpha insert replaced the viral VP1 protein coding sequence and the beta LH insert replaced the viral VP2 coding sequence.

Figure 10:
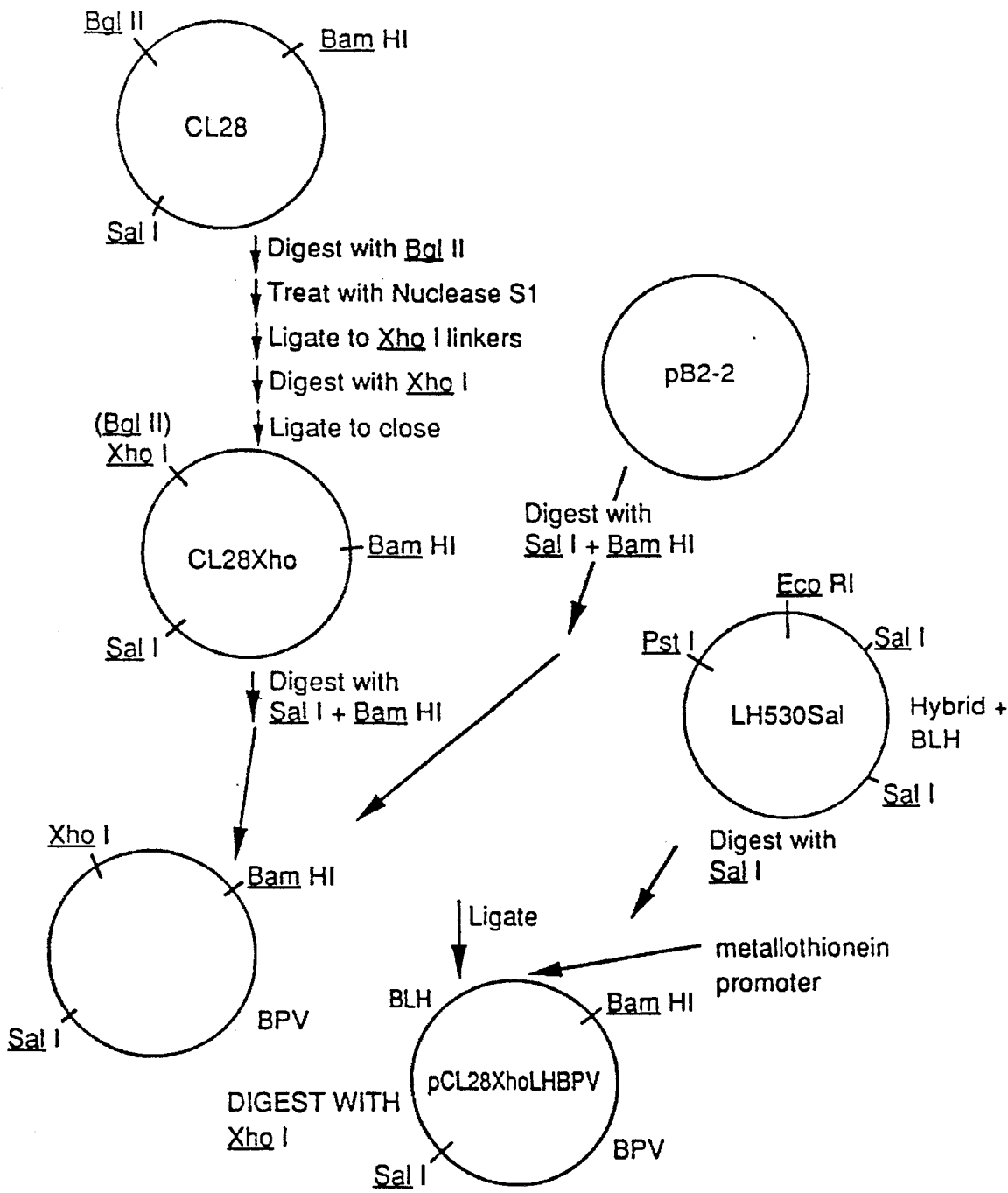
FIG. 10 is a diagrammatic illustration of the construction of the BPV-containing plasmid pCL28XhoLHBPV, encoding the beta subunit of LH.
Figure 11:
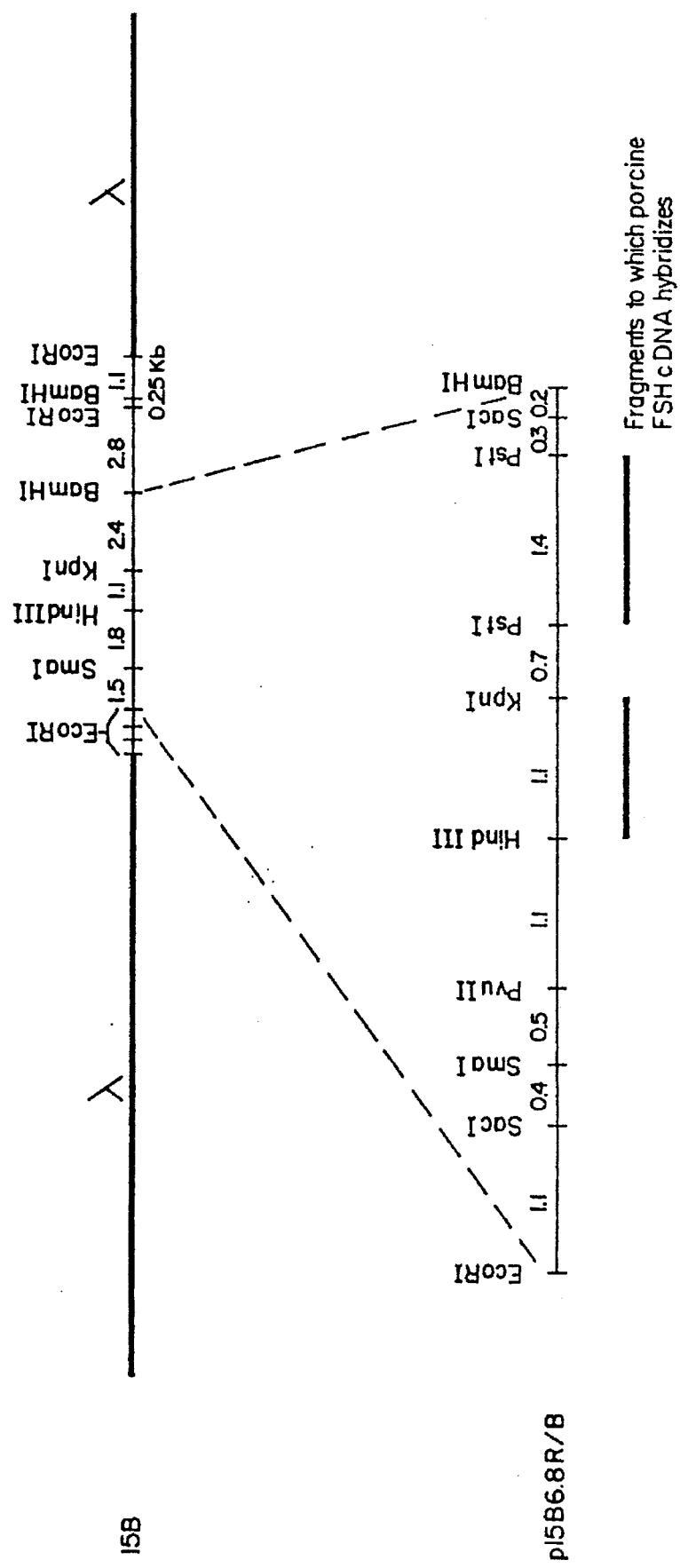
FIG. 11 is a partial restriction map of the lambda clone 15B and the beta FSH-containing 6.8 kb EcoRI-BamHI fragment that is inserted into pBR322.
Figure 12:
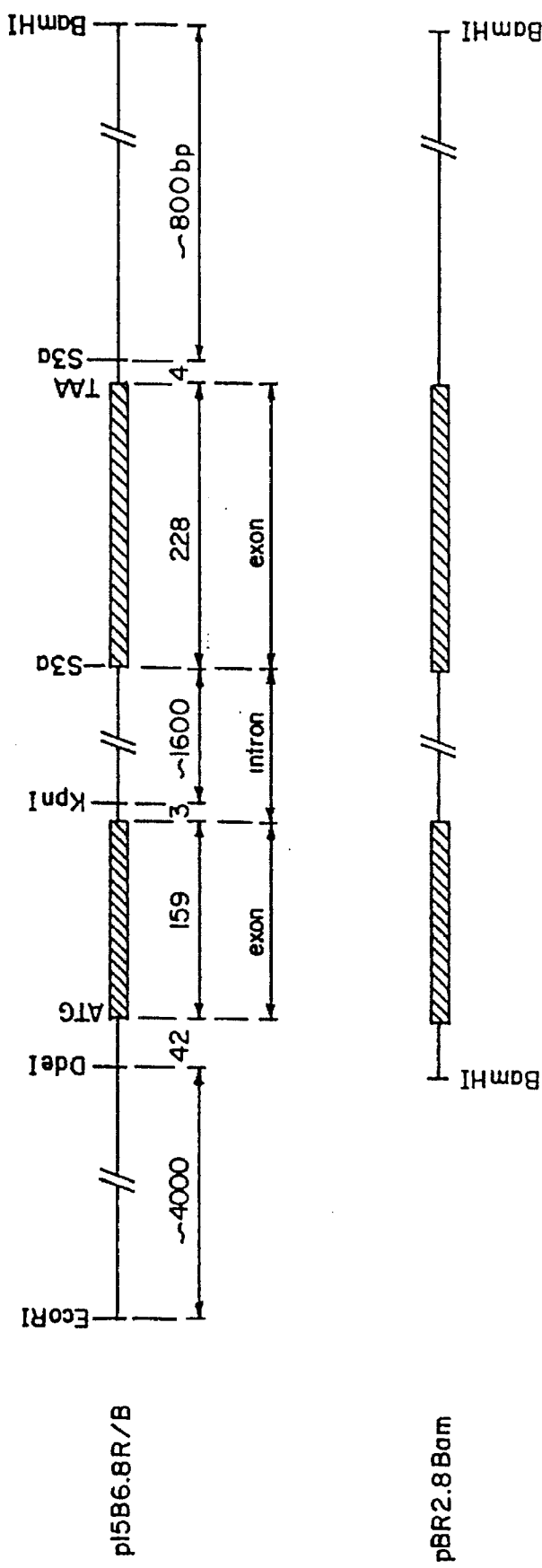
FIG. 12 is a partial restriction map of the beta FSH coding region and the BamHI fragment that is inserted into a BPV based expression vector.
Figure 13:
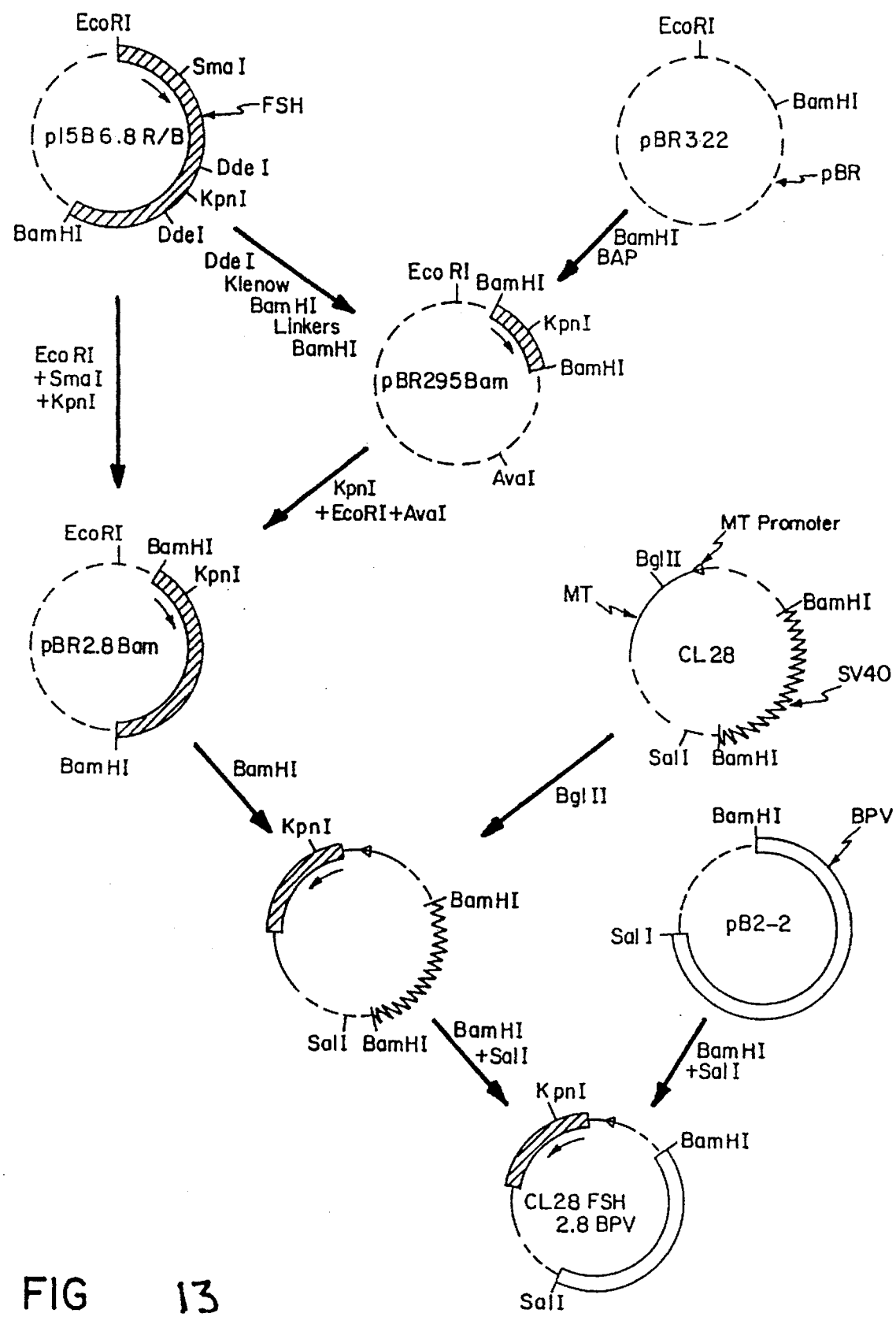
FIG. 13 is a diagrammatic illustration of the construction of the BPV-containing plasmid CL28FSH2.8BPV, encoding the beta subunit of FSH.

Insertion of the Beta LH cDNA (With Beta hCG 5' End of Signal Peptide) into a BPV-Based Expression System LH 520 H/B (FIG. 8) is digested with HindIII and BamHI, treated with the *E. coli* DNA polymerase (Klenow), ligated to synthetic SalI linkers, digested with SalI, and cloned into the SalI site of pBR322. The resulting plasmid, LH 530 Sal, is used as a source of the LH cDNA clone for insertion into the mouse metallothionein gene of the plasmid CL28 as described in FIG. 10.

CL28 is cut with BslII, treated with nuclease S1, and ligated to XhoI linkers. Following digestion with XhoI, ligation and digestion with BslII, *E. coli* is transformed with the reaction mix to give the plasmid CL28Xho. This plasmid is digested with BamHI and SalI and ligated to a BamHI plus 8alI digest of the plasmid pB2-2 (FIG. 4) to give the plasmid CL28XhoBPV. The latter LH insert is then ligated into the XhoI site of CL28XhoBPV as a SalI fragment, since the 5' overhang of SalI digests is complementary to that of XhoI digests. Following digestion with XhoI to eliminate background, *E. coli* is transformed and the desired plasmid pCL28XhoLHBVP containing the (hybrid) pre-beta LH insert, in a BPV-based plasmid, under control of the mouse metallothionein promoter, is isolated.

Transfection and Infection of Host Monkey Cells

The incorporation of virus-containing vectors into eukaryotic cells for the production of a heteropolymeric protein is generally accomplished as follows. First, if the viral DNA and homopolymeric protein-encoding DNA are incorporated into a plasmid, which is maintained, in, say, *E. coli*, the plasmid sequences (e.g. the pBR322 sequences) are removed and the resulting DNA is ligated to form circular DNA including the viral region and the heteropolymeric protein-encoding sequence or sequences. This circular DNA generally does not contain all of the genetic information needed to produce a replicating virus, the other necessary sequences (e.g. those encoding coat protein) having been replaced by the heteropolymeric protein-encoding sequence or sequences. The circular DNA, minus the plasmid DNA, must be close enough in size to the naturally occurring viral DNA from which it is derived to permit the DNA to enter and replicate in appropriate host mammalian cells.

The circular DNA is used to transfect host cells in order to produce virus stock for later infections. Since some of the DNA necessary to produce virus is missing, the transfection must occur in conjunction with helper virus DNA encoding enough of the missing function to produce replicating virus.

Transfected host cells are grown and incubated until lysed by replicating virus. The resulting replicating virus stock, including helper virus, is then used to infect host cells for production of the heteropolymeric protein. Virus stock is maintained, since it generally needs to be reused to infect fresh batches of host cells, as each culture of infected, protein-producing host cells generally is eventually lysed by the virus.

The specific recombinant DNA sequences described above are used to transfect, and then infect, host cells, as follows.

The pBR322 sequences are removed from the above-described SV40-containing plasmids to produce transfecting viral DNA. In the case of p alpha SVHVP1 and p alpha beta SVVPI, this is accomplished by digestion with BamHI, followed by ligation under conditions favoring circularization of the fragments to give (among other products) alpha SVHVP1 and alpha beta SVVPI. For p beta 8VVP1, digestion with EcoRI followed by re-ligation brings the SV40 late promoter and VP1 splice region into juxtaposition with the beta hCG cDNA insert at the same time that it eliminates pBR322 sequences and forms beta SVP1. At the same time, PtsA58 Bam (tsA58 SV40 viral DNA cloned into the pBR322 BamHI site) is cut with BamHI and ligated to obtain self-ligated circles. Analogous methods are used for the LH vectors. Separate virus stocks are prepared as described below.

The DNA's, which are cut and ligated as described above, are ethanol precipitated and dissolved in sterile water. Approximately 1 µg of ptsA58 Bam DNA (helper virus) and 10 µg of recombinant DNA (encoding alpha and/or beta hCG or LH) are combined in a sterile test tube, mixed with 2 ml of TBS buffer (G. Kimura and R. Dulbecco 1972, Virology, 49, 79–81) and 1 ml of 2 mg/ml DEAE-dextran solution and added to a monolayer of confluent monkey CV-1 cells previously washed twice with 10 ml of TBS in a T-75 flask. The cells are left at 37° C. for 1–2 hrs with occasional shaking, washed with TBS twice, fed with 10 ml of DMEM containing 5% fetal calf serum, and left at 40° C. for 10–15 days. After complete cell lysis, the medium is transferred to a test tube, frozen and thawed five times, and centrifuged at 3000 rpm for five minutes. The resulting supernatants serve as virus stocks for infection of fresh SV-1 cells.

To accomplish an infection, CV-1 cells are grown to confluence in a T-150 flask. 1 ml of one of the virus stocks (made as described above) is added to the flask and the cells are incubated at 40° C. for 5 days.

For mixed infections, CV-1 cells are grown to confluence in a T-150 flask, alpha SVHVPl and beta SVVI viruses are mixed in a 1:1 ratio and 1 ml of the mixed virus is used to infect CV-1 cells at 40° C.

Transfection of Mouse Cells

To produce heterodimeric hCG using a mixed transfection, five µg of each BPV plasmid, i.e., pRF 375 (alpha hCG) and pRF 398 (beta hCG), are mixed and added to 0.5 ml of a 250 mM $CaCl_2$ solution containing 10 µg of salmon sperm DNA as carrier. This mixture is bubbled into 0.5 ml of 280 mM NaCl, 50 mM Hepes and 1.5 mM sodium phosphate. The calcium phosphate precipitate is allowed to form for 30–40 minutes at room temperature.

24 hours prior to transfection, $5 \times 10^5$ cells of mouse C127 cells (available from Dr. Dean Hamer, National Cancer Institute, NIH, Bethesda, Md.) are placed in a 100 mm dish or T-75 flask. Immediately before adding the exogenous DNA, the cells are fed with fresh medium (Dulbecco's Modified Medium, 10% fetal calf serum). One ml of calcium phosphate precipitate is added to each dish (10 ml), and the cells are incubated for 6–8 hours at 37° C.

The medium is aspirated and replaced with 5 ml of 20% glycerol in phosphate buffered saline, pH 7.0 (PBS) for 2 minutes at room temperature. The cells are washed with PBS, fed with 10 ml of medium, and incubated at 37° C. After 20–24 hours, the medium is changed and subsequent refeeding of the cells is carried out every 3–4 days. Individual clones are grown in T-25 cm flasks. After 7–21 days, cell clones can be transferred to larger flasks for analysis.

To produce heterodimeric hCG using a single transfection, plasmid RF 398 alpha $t_2$ is employed in the same manner as the above two plasmids were employed for a mixed infection.

To make heterodimeric LH, plasmids pRF 375 and pCL28XhoLHBPV are mixed, as described above in the case of hCG.

An interesting observation is that culturing cells containing beta hCG or beta LH-encoding vectors alone, in the absence of alpha-encoding cells, produces practically no beta subunit, while cells containing alpha and beta-encoding sequences produce not only heterodimer, but free beta subunit as well. This lends support to the notion that the production of both subunits in a single cell culture has the additional advantage of somehow permitting the presence of the alpha subunit to stabilize the beta subunit.

A further interesting observation was that mouse C127 cells transformed by an expression vector for the alpha subunit of hCG, without the additional vector for the beta subunit, produces an alpha subunit which will not associate with the complementary urinary beta subunit (combination<5%). The recombinant alpha subunit apparently has more glycosylations than the native subunit and is thus prevented from combining with beta subunit to produce a biologically active hormone. However, when both subunits are produced by the same cells, proper association and glycosylation occurs in vivo so that biologically active hormone substantially identical to the native hormone is expressed.

Isolation of the Human beta FSH Gene

A human genomic library in phage lambda (Lawn et al., Cell, 15, 1157–1174 (1978)) is screened using "guessed" long probes. The idea behind such probes, set forth in Jaye et al., Nucleic Acids Research, 11, 2325 (1983), is that if the amino acid sequence of a desired protein is at least partially known, a long probe can be constructed in which educated guesses are made as to the triplet encoding any amino acid which can be encoded by more than one, and not more than four, different triplets. Any correct guesses increase the amount of homology, and improve the specificity, of the results.

To isolate desired regions of DNA, two labeled 45-mer probes are used: TB36, homologous with amino acids 56–70 of human beta FSH; and TB21, homologous with amino acids 73–87. These probes have the following nucleotide compositions (corresponding amino acids are also given):

TB36:        Val—Tyr—Glu—Thr—Val—Lys—Val—
(AA56–70) 3' CAC ATG CTC TGG CAC TCT CAC

Pro—Gly—Cys—Ala—His—His—Ala—Asp
             GGT CCG ACG CGG GTG GTG CGA CTG 5'

TB21:        Tyr—Thr—Tyr—Pro—Val—Ala—Thr—
(AA73–87) 3' ATG TGC ATG GGT CAC CGA TGT

Glu—Cys—His—Cys—Gly—Lys—Cys—Asp
             CTC ACA GTG ACG CCG TTT ACG CTG 5'

The above probes are used to screen the human genomic library as follows. TB21 is labeled with $^{32}P$ and used to screen approximately $5 \times 10^5$ lambda plaques on duplicate filters by the in situ plaque hybridization technique of Benton and Davis, Science, 196, 180–182 (1977). The prehybridization solution is maintained at 55° C. for several hours and has the following composition: 0.75M NaCl; 0.15M Tris/HCl, pH 8.0; 10 mM EDTA; 5×Denhardt's Solution; 0.1% sodium pyrophosphate; 0.1% SDS; 100 microgram/ml E. coli t-RNA. The hybridization solution has the same composition except that it is maintained overnight at 45° C., and contains labeled probe in a concentration of about $0.5 \times 10^6$ cpm/ml. After hybridization, the filters are washed four times in 1×SSC (=0.15M NaCl, 0.015M $Na_3$-citrate) and exposed to x-ray film.

This screening procedure yields 50 plaques which hybridize to TB21 on both sets of filters. These 50 individual plaques are picked and combined into 10 culture pools containing 5 plaques each. The 10 cultures are grown and DNA is isolated from 50 ml phage lysates. This DNA is then digested with EcoRI and fractionated on two identical 1% agarose gels, after which it is transferred to nitrocellulose paper according to the method of Southern, *J. Mol. Biol.*, 98, 503–517 (1975).

The DNAs on the two filters are hybridized to $^{32}$P labeled TB21 and TB36, respectively. Individual plaques from the pool containing a restriction fragment which strongly hybridizes to both probes are then screened according to the above procedure, except that the DNAs are digested with EcoRI, BamHI, and EcoRI plus BamHI. In this way the 6.8 kb EcoRI-BamHI fragment containing human beta FSH is isolated.

A partial restriction map of clone 15B, containing the 6.8 kb EcoRI-BamHI fragment is shown in FIG. 2. In order to locate the position of the beta FSH sequences within the clone, the 6.8 kb EcoRI-BamHI fragment of clone 15B is subcloned into pBR322 to yield plasmid p15B6.8R/B (FIG. 2). p15B6.8R/B is then digested with various restriction enzymes and the products are fractionated by agarose gel electrophoresis using conventional methods. The DNA is blotted to nitrocellulose paper and hybridized to fragments of a porcine beta FSH cDNA clone labeled with $^{32}$P by nick translation.

As shown in FIG. 2, the porcine beta FSH-probe hybridizes to only two fragments of the human DNA, namely a 1.1 kb HindIII-KpnI and a 1.4 kb PstI fragment. Partial DNA sequencing of these two fragments shows that this DNA indeed codes for human beta FSH and that the entire coding region for beta FSH is contained in these two fragments.

As shown by the restriction map of FIG. 3, the beta FSH coding sequence is interrupted by an intervening sequence of approximately 1.6 kb between amino acids 35 and 36 of mature beta FSH. The nucleotide sequence of the entire human beta FSH coding region and some of the flanking and intervening sequences are given below. The amino acid sequence deduced from the nucleotide sequence is given for the coding region.

```
                                    30                                              60
GCT TAC ATA ATG ATT ATC GTT CTT TGG TTT CTC AGT TTC TAG TGG GCT TCA TTG TTT GCT 90                                             120
TCC CAG ACC AGG |ATG| AAG ACA CTC CAG TTT TTC TTC CTT TTC TGT TGC TGG AAA GCA ATC
                |Met| Lys Thr Leu Gln Phe Phe Phe Leu Phe Cys Cys Trp Lys Ala Ile 150                                             180
TGC TGC (AAT) AGC TGT GAG CTG ACC AAC ATC ACC ATT GCA ATA GAG AAA GAA GAA TGT CGT
Cys Cys (Asn) Ser Cys Glu Leu Thr Asn Ile Thr Ile Ala Ile Glu Lys Glu Glu Cys Arg

210                          ↓                  240
TTC TGC ATA AGC ATC AAC ACC ACT TGG TGT GCT GGC TAC TGC TAC ACC AGG GTA GGT ACC
Phe Cys Ile Ser Ile Asn Thr Thr Trp Cys Ala Gly Tyr Cys Tyr Thr Arg 270                                             300
// ATG TTA GAG CAA GCA GTA TTC AAT TTC TGT CTC ATT TTG ACT AAG CTA AAT AGG AAC

330              ↓                              360
TTC CAC AAT ACC ATA ACC TAA CTC TCT TCT TAA ACT CCT CAG GAT CTG GTG TAT AAG GAC
                                                        Asp Leu Val Tyr Lys Asp 390                                             420
CCA GCC AGG CCC AAA ATC CAG AAA ACA TGT ACC TTC AAG GAA CTG GTA TAT GAA ACA GTG
Pro Ala Arg Pro Lys Ile Gln Lys Thr Cys Thr Phe Lys Glu Leu Val Tyr Glu Thr Val 450                                             480
AGA GTG CCC GGC TGT GCT CAC CAT GCA GAT TCC TTG TAT ACA TAC CCA GTG GCC ACC CAG
Arg Val Pro Gly Cys Ala His His Ala Asp Ser Leu Tyr Thr Tyr Pro Val Ala Thr Gln 510                                             540
TGT CAC TGT GGC AAG TGT GAC AGC GAC AGC ACT GAT TGT ACT GTG CGA GGC CTG GGG CCC
Cys His Cys Gly Lys Cys Asp Ser Asp Ser Thr Asp Cys Thr Val Arg Gly Leu Gly Pro

570
AGC TAC TGC TCC TTT GGT GAA ATG AAA GAA |TAA| AAA TCA GTG GAC ATT TC
Ser Tyr Cys Ser Phe Gly Glu Met Lys Glu
```

Still referring to the above sequence, there is a box around the ATG initiation codon of the 18 amino acid signal peptide, which is cleaved post-translationally. The mature protein begins with the amino acid Asn encoded by the circled triplet AAT. The exon-intron boundaries are marked by arrows; they are flanked by the consensus sequence GT for the splice donor and AG for the splice acceptor site. There is a box around the stop codon TAA, the end of the coding region.

Below is a reproduction of the above sequence not broken into triplets, showing restriction sites; the ATG beginning and the TAA ending the coding region are boxed and the exon-intron junctions are marked by arrows.

```
         10         20         30         40         50         60
GCTTACATT TGATTATCGT TCTTTGGTTT CTCAGTTTCT AGTGGGCTTC ATTGTTTGCT
                              D
                              D
                              E
                              1

70         80         90        100        110        120
TCCCAGACCA GGATGAAGAC ACTCCAGTTT TTCTTCCTTT TCTGTTGCTG GAAAGCAAT C
           B  F  M                    M
           S  O  B                    B
           T  K  O                    O
           1  1  2                    2

130        140        150        160        170        180
TGCTGCAATA GCTGTGAGCT GACCAACATC ACCATTGCAA TAGAGAAAGA AGAATGTCGT
      B          A          A          H                   H
      B          L          L          P                   B
      V          U          U          H                   O
      1          1          1          1                   2

190        200        210        220        230 ↓      240
TTCTGCATAA GCATCAACAC CACTTGGTGT GCTGGCTACT GCTACACCAG GGTAGGTACC
           S                                           B       KR
           F                                           S       PS
           A                                           T       NA
           1                                           1       11

250        260        270        280        290        300
// ATGTTAG AGCAAGCAGT ATTCAATTTC TGTCTCATTT TGACTAAGCT AAATAGGAAC
                                            D  A
                                            D  L
                                            E  U
                                            1  1

310        320        330        340 ↓      350        360
TTCCACAATA CCATAACCTA ACTCTCTTCT TAAACTCCTC AGGATCTGGT GTATAAGGAC
              M                     S D    X S             A
              B                     A D    H A             V
              O                     U E    O U             A
              2                     1 1    2 A             2

370        380        390        400        410        420
CCAGCCAGGC CCAAAATCCA GAAAACATGT ACCTTCAAGG AACTGGTATA TGAAACAGTG
      B  S                  A  R
      S  A                  F  S
      T  U                  L  A
      1  1                  3  1

430        440        450        460        470        480
AGAGTGCCCG GCTGTGCTCA CCATGCAGAT TCCTTGTATA CATACCCAGT GGCCACCCAG
    N H      H  H         H          S               B H
    C P      G  P         I          N               A A
    I A      I  H         N          A               L E
    1 2      1  1         1          1               1 3

490        500        510        520        530        540
TGTCACTGTG GCAAGTGTGA CAGCGACAGC ACTGATTGTA CTGTGCGAGG CCTGGGGCCC
                                      R              M S H  B     A S
                                      S              N T A  S     P A
                                      A              L UE   T     A U
                                      A              1 13   1     1 1

550        560        570        580        590
AGCTACTGCT CCTTTGGTGA AAT GAAAGAA TAAA GATCAG TGGACATTTC
A          H                      S
L          P                      A
U          H                      U
1          A                      A
```

Insertion of the Beta FSH DNA into a BPV-Based Expression Vector

Referring to FIG. 3, a synthetic BamHI linker is inserted at the DdeI site of p15B6.8R/B, which is located 42 nucleotides 5. of the ATG initiation codon. Referring to FIG. 4, p15B6.8R/B is digested with DdeI and treated with E. coli DNA polymerase (Klenow), after which it is ligated to synthetic BamHI linkers and digested with BamHI. The 295 bp fragment containing the first exon of FSH is isolated and cloned into the BamHI site of pBR322. The resulting plasmid pBR295Bam is digested with KpnI plus EcoRI plus AvaI and ligated to p15B6.8R/B which has been digested with KpnI plus EcoRI plus SmaI. The ligation mix is then used to transform *E. coli*, and the plasmid pBR2.8Bam containing the human beta FSH DNA sequence as a BamHI fragment is identified from among the transformants by restriction mapping.

As shown in FIG. 4, expression plasmid CL28FSH2.8BPV is prepared according to the same method used to prepare pRF375 (FIG. 1), except that the 2.8 kb BamHI fragment of pBR2.8Bam is used in place of the alpha hCG cDNA clone. Plasmid CL28FSH2.8BPV can be used to transform mammalian host cells using conventional methods, and human beta FSH can be isolated and purified.

Transfection of Mouse Cells

To produce heterodimeric FSH using a mixed transfection, five µg of each BPV plasmid, i.e., pRF375 (alpha subunit) and CL28FSH2.8BPV (beta FSH), are mixed and added 0.5 ml of a 250 mM $CaCl_2$ solution containing 10 µg of salmon sperm DNA as carrier. This mixture is bubbled into 0.5 ml 280 mM NaCl, 50 mM Hepes and 1.5 mM sodium phosphate. The calcium phosphate precipitate is allowed to form for 30–40 minutes at room temperature.

24 hours prior to transfection, $5 \times 10^5$ cells of mouse C127 cells (available from Dr. Dean Hamer, National Cancer Institute, NIH, Bethesda, Md.) are placed in a 100 mm dish or T-75 flask. Immediately before adding the exogenous DNA, the cells are fed with fresh medium (Dulbecco's Modified Medium, 10% fetal calf serum). One ml of calcium phosphate precipitate.e is added to each dish (10 ml), and the cells are incubated for 6–8 hours at 37° C.

The medium is aspirated and replaced with 5 ml of 2 glycerol in phophate buffered saline, pH 7.0 (PBS) for 2 minutes at room temperature.

The cells are washed with PBS, fed with 10 ml of medium, and incubated at 37° C. After 20–24 hours, the medium is changed and subsequent refeeding of the cells is carried out every 3–4 days. Individual clones are grown in T-25 flasks. After 7–21 days, cell clones can be transferred to larger flasks for analysis.

Deposits

The following, described above, have been deposited in the American Type Culture Collection, Rockville, Md.:

alpha beta SVVP1, ATCC VR 2077;
alpha SVHVP1, ATCC VR 2075;
beta SVVP1, ATCC VR 2075;
pRF 375 in C127 cells, ATCC CRL 8401;
pRF 398 in C127 cells, ATCC CRL 8401;
pCL28XhoLHBPV *E. coli*, ATCC 39475;
pRF 398 alpha $t_2$ in C127 cells, ATCC CL 8400.

The following, described above, has been deposited in the Agricultural Research Culture Collection (NRRL), Peoria, Ill. 61604:

CL28FSH2.8BPV in *E. coli*, NRRL B-5923.

Use

The transformed cell lines of the invention are used to produce glycosylated biologically active heterodimeric human fertility hormones. hCG and LH made according to the invention, for example, have a number of well-known medical uses associated with human fertility. Furthermore, FSH can be used, alone or in conjunction with hCG or LH, to induce ovulation or superovulation for in vitro fertilization. In addition, heterodimeric FSH, or the beta subunit alone, can be used in diagnostic tests for fertility and pituitary functions.

Human fertility hormones produced by recombinant cells have the advantage, compared to such hormones obtained from natural sources, of being free from contamination by other human proteins, in particular other fertility hormones.

Other Embodiments

Other host cells, vectors, promoters, transforming sequences, and viruses can also be employed. The host cell employed generally is dependent on the vector being used. For example, when the vector is a replicating virus or a non-replicating viral DNA, the host cells are cells capable of being infected or transfected, respectively, by those vectors; e.g., SV40-containing vectors require monkey host cells, preferably CV-1 cells. Where the cloning vector is a plasmid having procaryotic control sequences, prokaryotic host cells, e.g., *E. coli*, are used. Where the cloning vector is a plasmid having eukaryotic control sequences, appropriate eukaryotic host cells, e.g., mouse C127 cells, are used. Besides autonomously replicating vectors, suitable vectors can be used to insert the DNA into the genome of the host cell, as is well known to those skilled in the art. As is also well known in the art, the vector may also contain an amplifiable marker, such as DHFR, particularly when used to transfect a DHFR⁻ CHO cell line.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

We claim:

1. A process for producing biologically active heterodimeric human fertility hormone selected from the group consisting of human chorionic gonadotropin, human luteinizing hormone and human follicle stimulating hormone, comprising:

transforming a eukaryotic cell with at least one vector constructed so as to insert into said cell DNA coding for each of the two subunits of the hormone, the translation of the DNA of each said subunit being controlled by a separate promoter; and culturing said cell under conditions appropriate to permit expression of the hormone therefrom, wherein said eukaryotic cell is one which permits appropriate post-translational modification of the subunits so produced such that the formed protein is biologically active.

2. A process in accordance with claim 1, wherein said hormone is human chorionic gonadotropin.

3. A process in accordance with claim 1, wherein said hormone is human luteinizing hormone.

4. A process in accordance with claim 1, wherein said hormone is human follicle stimulating hormone.

5. A process in accordance with claim 1, wherein said transforming step comprises transforming the cell with a single vector containing DNA for both of said subunits under the control of separate promoters.

6. A process in accordance claim 1, wherein said transforming step comprises transforming the cell with two vectors each containing DNA for one of said subunits and an appropriate promoter.

7. A process in accordance with claim 1, wherein said at least one vector is autonomously replicating.

8. A process in accordance with claim 1, wherein said at least one vector is a plasmid or a replicating virus.

9. A process in accordance with claim 1, wherein each of said promoters are different.

10. A eukaryotic cell transformed by at least one vector constructed so as to insert into said cell heterologous DNA coding for each of the two subunits of a heterodimeric human fertility hormone selected from the group consisting of human chorionic gonadotropin, human luteinizing hormone and human follicle stimulating hormone, the translation of the DNA of each said subunit being controlled by a separate promoter, said eukaryotic cell being of a species which permits appropriate post-translational modification of the subunits so produced such that the formed protein is biologically active.

11. A cell in accordance with claim 10, wherein said hormone is human chorionic gonadotropin.

12. A cell in accordance with claim 10, wherein said hormone is human luteinizing hormone.

13. A cell in accordance with claim 10, wherein said hormone is human follicle stimulating hormone.

14. A cell in accordance with claim 10, wherein the cell has been transformed with a single vector containing DNA for both of said subunits under the control of separate promoters.

15. A cell in accordance with claim 10, wherein the cell has been transformed with two vectors each containing DNA for one of said subunits and an appropriate promoter.

16. A cell in accordance with claim 10, wherein said at least one vector is autonomously replicating.

17. A cell in accordance with claim 10, wherein said at least one vector is a plasmid or a replicating virus.

18. A cell in accordance with claim 10, wherein each of said promoters are different.

19. An expression vector containing DNA encoding each of the two subunits of a heterodimeric human fertility hormone selected from the group consisting of human chorionic gonadotropin, human luteinizing hormone and human follicle stimulating hormone, with separate promoters for each said subunit.

20. An expression vector in accordance with claim 19, wherein said hormone is human chorionic gonadotropin.

21. An expression vector in accordance with claim 19, wherein said hormone is human luteinizing hormone.

22. An expression vector in accordance with claim 19, wherein said hormone is human follicle stimulating hormone.

23. An expression vector in accordance with claim 19, wherein each said promoter is different.

24. An expression vector in accordance with claim 23, wherein said two different promoters are derived from two different species.

25. An expression vector in accordance with claim 19, which is autonomously replicating.

26. An expression vector in accordance with claim 19 comprising a plasmid or a replicating virus.

* * * * *